United States Patent
Chien et al.

(10) Patent No.: US 6,416,944 B1
(45) Date of Patent: Jul. 9, 2002

(54) METHODS OF TYPING HEPATITIS C VIRUS AND REAGENTS FOR USE THEREIN

(75) Inventors: David Y. Chien, Alamo; George Kuo, San Francisco, both of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/439,157

(22) Filed: May 11, 1995

Related U.S. Application Data

(62) Division of application No. 08/336,553, filed on Nov. 9, 1994, now Pat. No. 6,054,264, which is a continuation of application No. 08/060,400, filed on May 10, 1993, now abandoned.

(51) Int. Cl.[7] .................................................. C12Q 1/70
(52) U.S. Cl. ................................ 435/5; 435/6; 436/820
(58) Field of Search ......................... 536/23.72; 435/5, 435/6; 436/820

(56) References Cited

U.S. PATENT DOCUMENTS

| | | | | |
|---|---|---|---|---|
| 4,868,105 A | | 9/1989 | Urdea et al. .................... | 435/6 |
| 5,106,726 A | | 4/1992 | Wang ............................. | 435/5 |
| 5,124,246 A | | 6/1992 | Urdea et al. .................... | 435/6 |
| 5,350,671 A | * | 9/1994 | Houghton et al. .............. | 435/5 |
| 5,427,909 A | * | 6/1995 | Okamoto ....................... | 435/54 |
| 5,527,669 A | * | 6/1996 | Resnick et al. ................. | 435/5 |

FOREIGN PATENT DOCUMENTS

| | | |
|---|---|---|
| EP | 318216 | 5/1989 |
| EP | 388232 | 9/1990 |
| EP | 0 586 065 A2 | 3/1994 |
| WO | 91/15771 | 10/1991 |
| WO | 93/00365 | 1/1993 |
| WO | 93/06247 | 4/1993 |
| WO | 93/10239 | 5/1993 |
| WO | 94/11388 | 5/1994 |
| WO | WO 94/25602 | 11/1994 |

OTHER PUBLICATIONS

Mondelli et al., Hepatitis C Virus (HCV) Core Serotypes in Chronic HCV Infection. Journal of Clinical Microbiology 32(10):2523–2527, 1994.*
Chan et al., Analysis of a new hepatitis C virus type and its phylogenetic relationship to existing variants, J. Gen. Virol. 73:1131–1141, 1992.*
Okamoto et al., Full–length Sequence of a Hepatitis C Virus Genome Having Poor Homology to Reported Isolates: Comparative Study of Four Distinct Genotypes, Virology 188:331–341, 1992.*
Chan et al., Serological responses to infection with three different types of hepatitis C virus, Lancet 338:1391, 1991.*
Cruse et al., *Illustrated Dictionary of Immunology*. CRC Press, Boca Raton, 1995, p. 258.*
Bhattacherjee et al., Use of NS–4 peptides to identify type–specific antibody to hepatitis C virus genotypes, 1, 2, 3, 4, 5 and 6. Journal of General Virology 76:1737–1748, 1995.*
Akbar et al., *Gastroenerologia Japonica* (1992) 27(4):514–520.
Allain et al., *Blood* (1991) 78(9):2462–2468.
Bradley et al., *Microbial Pathogenesis* (1992) 12(6):391–398.
Brown et al., *J. Med. Virol.* (1992) 38(3):167–171.
Cerino and Mondelli, *J. Immunol.* (1991) 147(8):2692–2696.
Cha et al., *PNAS* (1992) 89:7144–7148.
Chen et al., *Virology* (1992) 188(1):102–113.
Choo et al., *Science* (1989) 244:359–362.
Choo et al., *Brit. Med. Bull* (1990) 46:423–441.
Choo et al, *PNAS* (1991) 88(6):2451–2455.
Finegold et al., *Diagnostic Microbiology*, 6th ed., C. V. Mosby Co., St. Louis, MO., (1982) p. 576.
Geysen *J. Trop. Med. Pub. Health* (1990) 21:523–533.
Hosada et al., *Gastroenterology* (1992) 102(3): 1039–1043.
Houghton et al., *Hepatology* (1991) 14:381–388.
Kanai et al, *Lancet* (1992) 339:1543.
Kato et al., *Biochem. Biophys. Res. Commun.* (1991) 181(1):279–285.
Kiyosawa et al., *JP Gastroenterologia Japonica* (1993) 28(4):63–68.
Kuo et al., *Science* . (1989) 244:362–364.
Lee et al., *J. Clin. Microb.* (1992) 30(6):1602–1604.
Lenzi et al., *Lancet* (1991) 338(8762):277–280.
Li et al., *J. Hepatology* (1991) 13(4):S33–7.
Li et al., *Gene* (1991) 105:167–172.
McOmish et al., *Transfusion* (1993) 33:7–13.
Merrified, *J. Am. Chem. Soc.* (1963) 85:2149–2154.
Mori et al., *Biochem. Biophys. Res. Commun.* (1992) 183:334–342.
Nakao et al., *J. Gen. Virol.* (1991) 9:2105–2112.
Okamoto et al., *J. Gen. Virol.* (1991) 72:2697–2704.
Okamoto et al., *J. Gen. Virol.* (1992) 73:673–679.
Pozzato et al., *Lancet* (1991) 338:59.
Roggendorf et al., *Archives of Virology* , (1993) 7:27–39.
Sallberg et al., *Imm. Letters* (1992) 33(1):27–34.
Sallberg et al., *Clin. Exp. Immunol.* (1993) 91(3):489–494.
Simmonds and Chan, *Molecular Virology: A Practicle Approach* (1993) p. 109–138.

(List continued on next page.)

Primary Examiner—Donna C. Wortman
(74) Attorney, Agent, or Firm—Roberta L. Robins; Alisa A. Harbin; Robert P. Blackburn

(57) ABSTRACT

The claimed invention provides methods of detecting and typing HCV using nucleic acid molecules encoding type specific and type-cluster specific epitopes. The nucleic acid molecules flanking regions encoding type specific or type cluster specific epitopes are useful in priming the polymerase chain reaction to determine the genotype an HCV isolate.

26 Claims, 4 Drawing Sheets

OTHER PUBLICATIONS

Simmonds et al., *J. Gen. Virol.* (1993) 74:661–668.
Simmonds et al., *J. Clin. Microbiology* 31:1493–1503.
Stuyver et al., *Biochem. and Biosphysical Res. Comm.* (1993) 192(2):635–641.
Takada et al., *Lancet* (1992) 339:808.
Takada et al., *J. Hepatology* (1992) 14(1):35–40.
Takamizwaa et al., *J. Virol.* (1991) 65:1105–1113.
Tsukiyama–Kohara et al., *Virology* (1993) 192(2):430–437.
Vallari et al., *J. Clin. Micro.* (1992) 30(3):552–556.
van Rijn, *Veterinary Microbiology* (1992) 33(1–4):221–230.
Weiner et al., *PNAS (USA )* (1992) 89(8):3468–3472.
Yoshioka et al., *Hepatology* (1992) 16:293–299.
Enomoto et al., *Biochem. Biophys. Res. Commun.* (1990) 170:1021–1025.

* cited by examiner

METHODS OF TYPING HEPATITIS C VIRUS AND REAGENTS FOR USE THEREIN

This application is a divisional, of application Ser. No. 08/336,553, filed Nov. 9, 1994 U.S. Pat. No. 6,054,264, which is a continuation of application Ser. No. 08/060,400, filed May 10, 1993, now abandoned.

FIELD OF THE INVENTION

This invention relates to typing hepatitis C viruses (HCV). In particular, this invention relates to a method of typing HCV using novel type specific polypeptides.

BACKGROUND OF THE INVENTION

Viral hepatitis is known to be caused by five different viruses known as hepatitis A, B, C, D and E. HAV is an RNA virus and does not lead to long-term clinical symptoms. HBV is a DNA virus. HDV is a dependent virus that is unable to infect cells in the absence of HBV. HEV is a water-borne virus. HCV was first identified and characterized as a cause of non-A, non-B hepatitis (NANBH). Houghton et al., EPO Pub. No. 388,232. This led to the disclosure of a number of general and specific polypeptides useful as immunological reagents in identifying HCV. See. e.g., Choo et al. (1989) *Science*, 244:359–362; Kuo et al. (1989) *Science*, 244:362–364; and Houghton et al. (1991) *Hepatology*, 14:381–388. HCV is the major cause of blood transfusion-related hepatitis.

The prototype isolate of HCV was characterized in EP Publication Nos. 318,216 and 388,232. As used herein, the term "HCV" includes newly isolated NANBH viral species. The term "HCV-1" refers to the virus described in the above-mentioned publications.

Since the initial identification of HCV, at least six different viral types have been identified and designated HCV-1 to HCV-6. Cha et al. (1992) *Proc. Natl. Acad. Sci. USA*, 89:7144–7148. Within these types are numerous subtypes. The type of virus with which a patient is infected may affect the clinical prognosis and also response to various treatments. Yoshioka et al. (1992) *Hepatology*, 16:293–299. In light of the fact that the most serious clinical outcome of HCV infection is hepatocellular carcinoma, it would be useful to be able to determine with which type or types of HCV a patient is infected.

The method currently in use to determine virus type is genotyping; that is, isolation of viral RNA and determination of the sequence of various segments by polymerase chain reaction (PCR). Not only is this method laborious and time consuming but it is not suitable for use on samples that have been stored under conditions that do not allow for preservation of RNA or samples from patients that do not have sufficient viral titer. It would be useful to have a method for typing HCV by immunoanalysis or serotyping.

The current method for screening blood and diagnosing patients is an immunoassay. The immunoassay utilizes an antigen from HCV-1 which contains a sufficient number of common epitopes to detect antibodies to other types of HCV. The immunoassay does not distinguish between infections by different types of HCV.

SUMMARY OF THE INVENTION

The present invention includes compositions and methods for typing of HCVs by genotype and serotype. The compositions include type specific epitopes, type-cluster specific epitopes, nucleic acids encoding the epitopes for use as probes and nucleic acids complementary to the regions flanking those encoding the epitopes for use as primers.

One aspect of the invention is a method for typing HCV comprising, the steps of providing an antibody-containing sample from an individual; contacting the sample with a type specific epitope or type-cluster specific epitopes under conditions which permit antigen-antibody binding; and determining whether antibodies in the sample bind to the epitope.

Another aspect of the invention relates to a method for typing HCV comprising the steps of providing an antibody-containing sample from an individual; contacting the sample with a first type specific epitope or type-cluster specific epitope under conditions which permit antigen-antibody binding; contacting the sample with a second type specific epitope or type-cluster specific epitope under conditions which permit antigen-antibody binding; and determining whether antibodies in the sample bind to either the first or second epitope.

Another aspect of the invention relates to polypeptides containing type specific epitopes or type-cluster specific epitopes. The polypeptides are derived from three different regions of the HCV genome. One set of polypeptides includes type specific epitope or type-cluster specific epitopes obtained from the HCV core region. This first set is found between amino acid residues sixty-seven and eighty-four of HCV-1 and homologous regions of other types of HCV. As used herein, the amino acid residue abbreviations are as follows: A, alanine; I, isoleucine; L, leucine; M, methionine; F, phenylalanine; P, proline; W,. tryptophan; V, valine; N, asparagine; C, cysteine; Q, glutamine; G, glycine; S. serine; T. threonine; Y, tyrosine; R, arginine; H, histidine; K, lysine; D, aspartic acid; and E, glutamic acid.

The particular amino acid residue sequences derived from the core region and subtypes from which they are derived are as follows:

1. PEGRTWAQ (SEQ ID NO:3), subtype 1a or 1b.
2. STGKSWGK (SEQ ID NO:4), subtype 2a or 2b.
3. SEGRSWAQ (SEQ ID NO:5), subtype 3a or 4.

Another set of polypeptides includes a type specific epitope obtained from the HCV non-structural region 4 (NS4). This second set is found between amino acid residues 1689–1718 of HCV-1 and homologous regions of other types of HCV.

The particular amino acid residue sequences and types or subtypes from which they are derived are as follows:

1. CSQHLPY (SEQ ID NO:5), subtype 1a.
2. CASHLPY (SEQ ID NO:7), subtype 1b.
3. CASRAAL (SEQ ID NO:8), subtype 2a or 2b.
4. CASKAAL (SEQ ID NO:23)

Another set of polypeptides includes type specific epitope or type-cluster specific epitopes obtained from the non-structural region 5 (NS5) of a hepatitis C virus. This set is found between amino acid residues 2281–2313 of HCV-1 and homologous regions of other types of hepatitis C virus.

The particular amino acid residue sequences and types or subtypes from which they are derived are as follows:

1. PDYEPPVVHG (SEQ ID NO:9), subtype 1a.
2. PDYVPPVVHG (SEQ ID NO:10), subtype 1b.
3. PDYQPATVAG (SEQ ID NO:11), subtype 2a.
4. PGYEPPTVLG (SEQ ID NO:12), subtype 2b.
5. FAQASPVW (SEQ ID NO:13), subtype 1a.
6. FPPQALPIW (SEQ ID NO:14), subtype 1b.
7. FPPQALPAW (SEQ ID NO:15), subtype 2a.
8. FPPQALPPW (SEQ ID NO:16), subtype 2b.

Another aspect of the invention includes nucleic acid molecules encoding the amino acid residue sequences of the type specific and type-cluster epitopes described. These nucleic acid molecules are useful as probes for instance in Southern blots or other DNA recognition assays such as the capture assay described in U.S. Pat. Nos. 4,868,105; and 5,124,246.

Another aspect of the invention includes nucleic acid molecules complementary to the nucleic acid sequences flanking regions encoding the type specific and type-cluster specific epitopes. Such nucleic acid molecules are useful: in performing PCR to determine the genotype of a particular HCV.

DEFINITIONS

Figure 1:
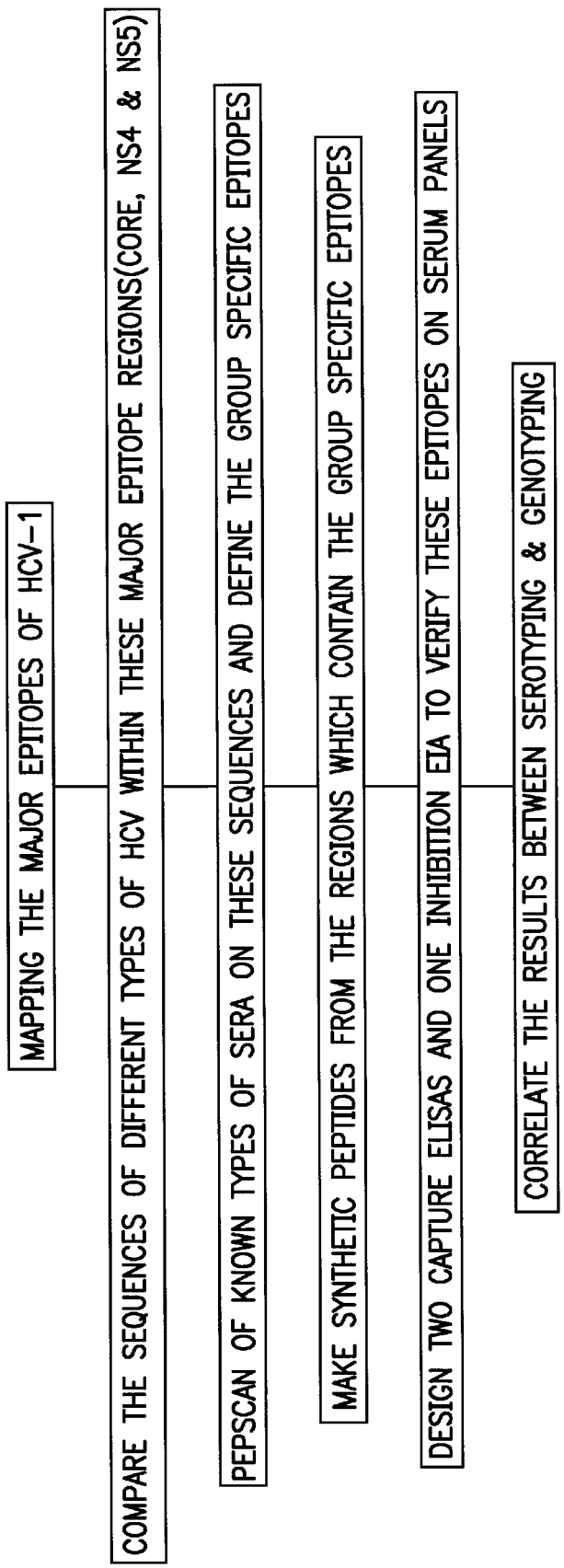
FIG. 1 is a flow diagram of the serotyping experimental strategy.
Figure 2:
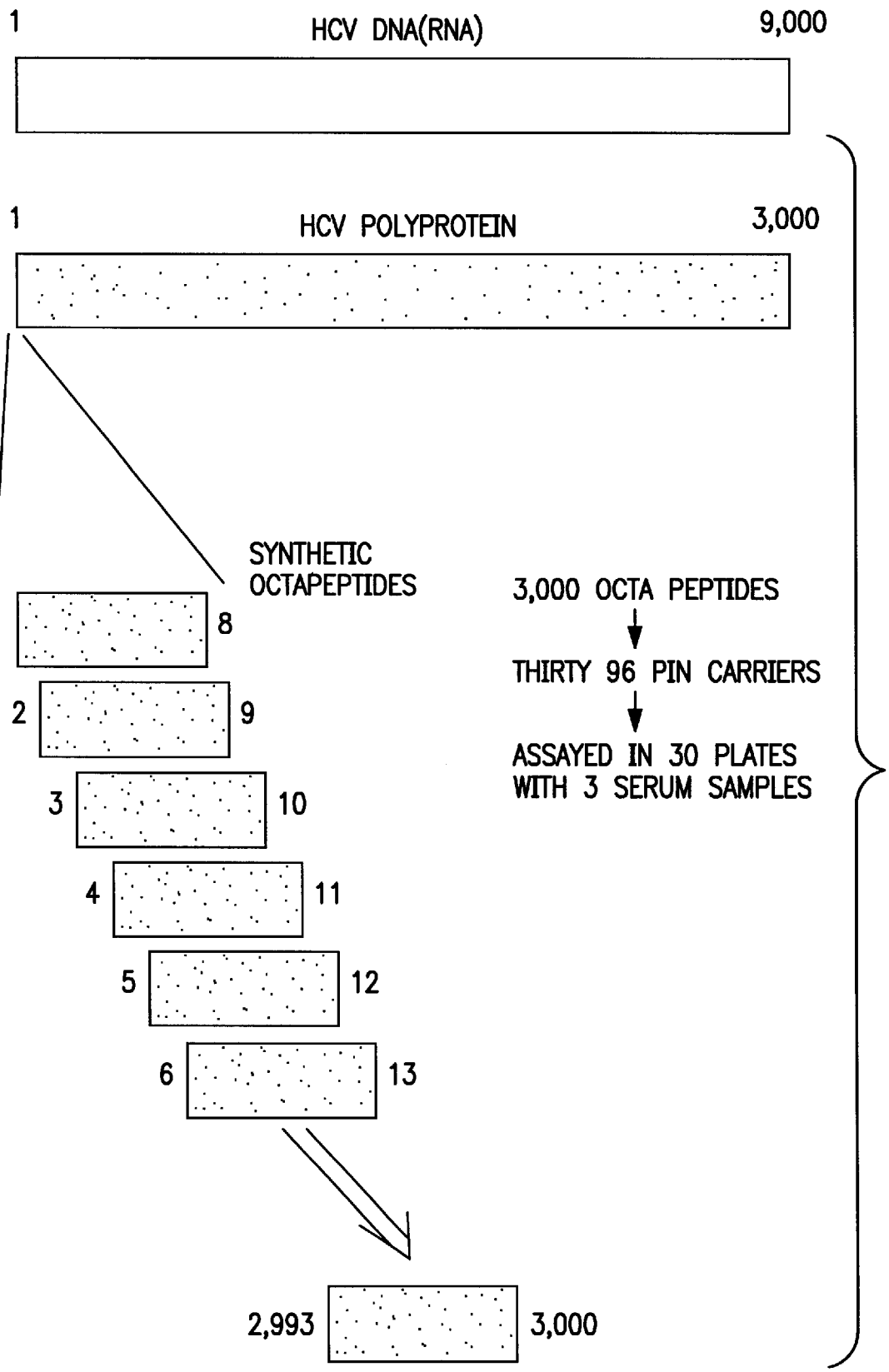
FIG. 2 is a flow diagram of the comprehensive epitope mapping strategy.
Figure 3:
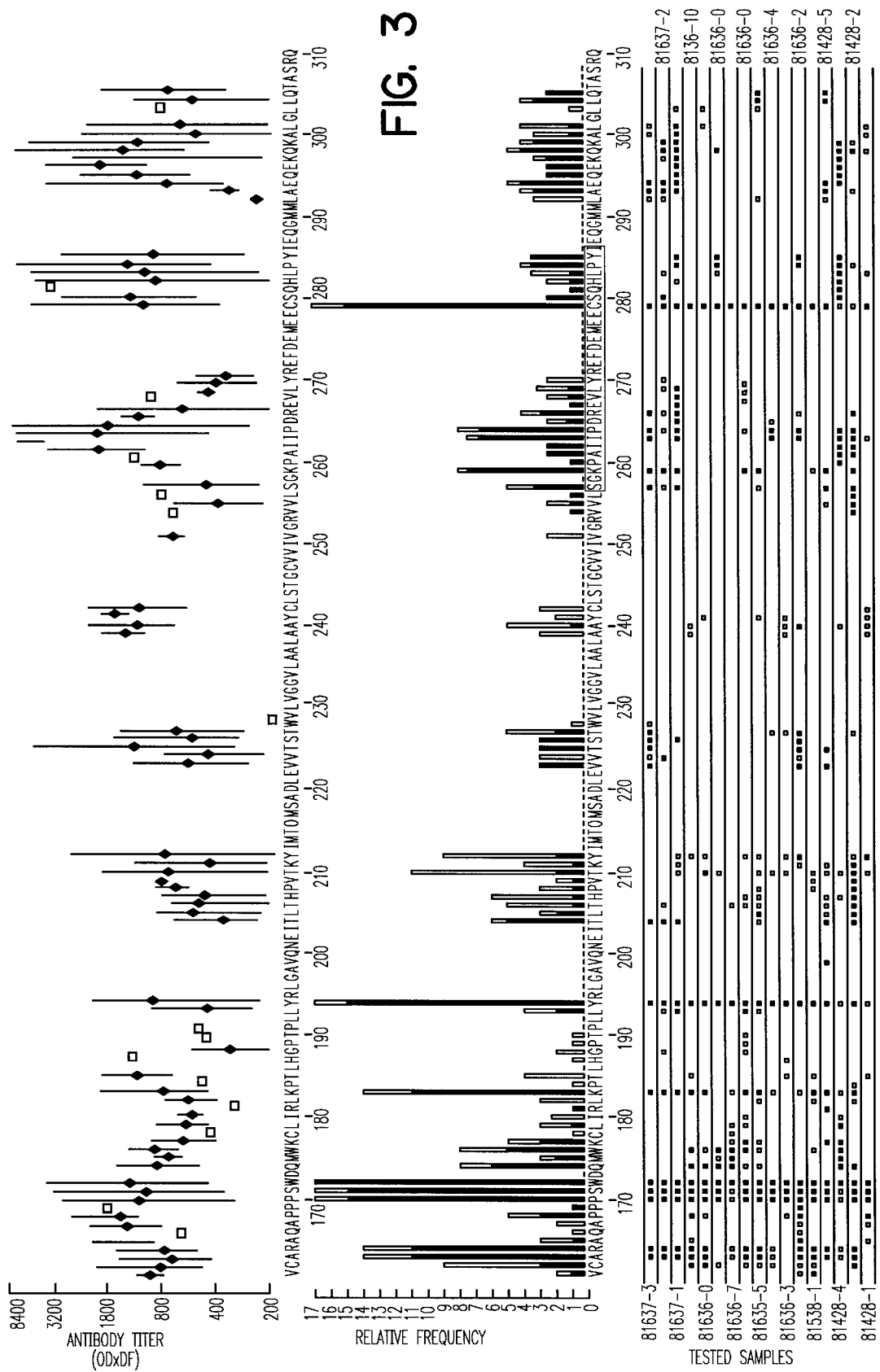
FIG. 3 (SEQ ID NO:1) is a compilation of graphs depicting the results of epitope mapping of HCV 1a (Rodney).
Figure 4:
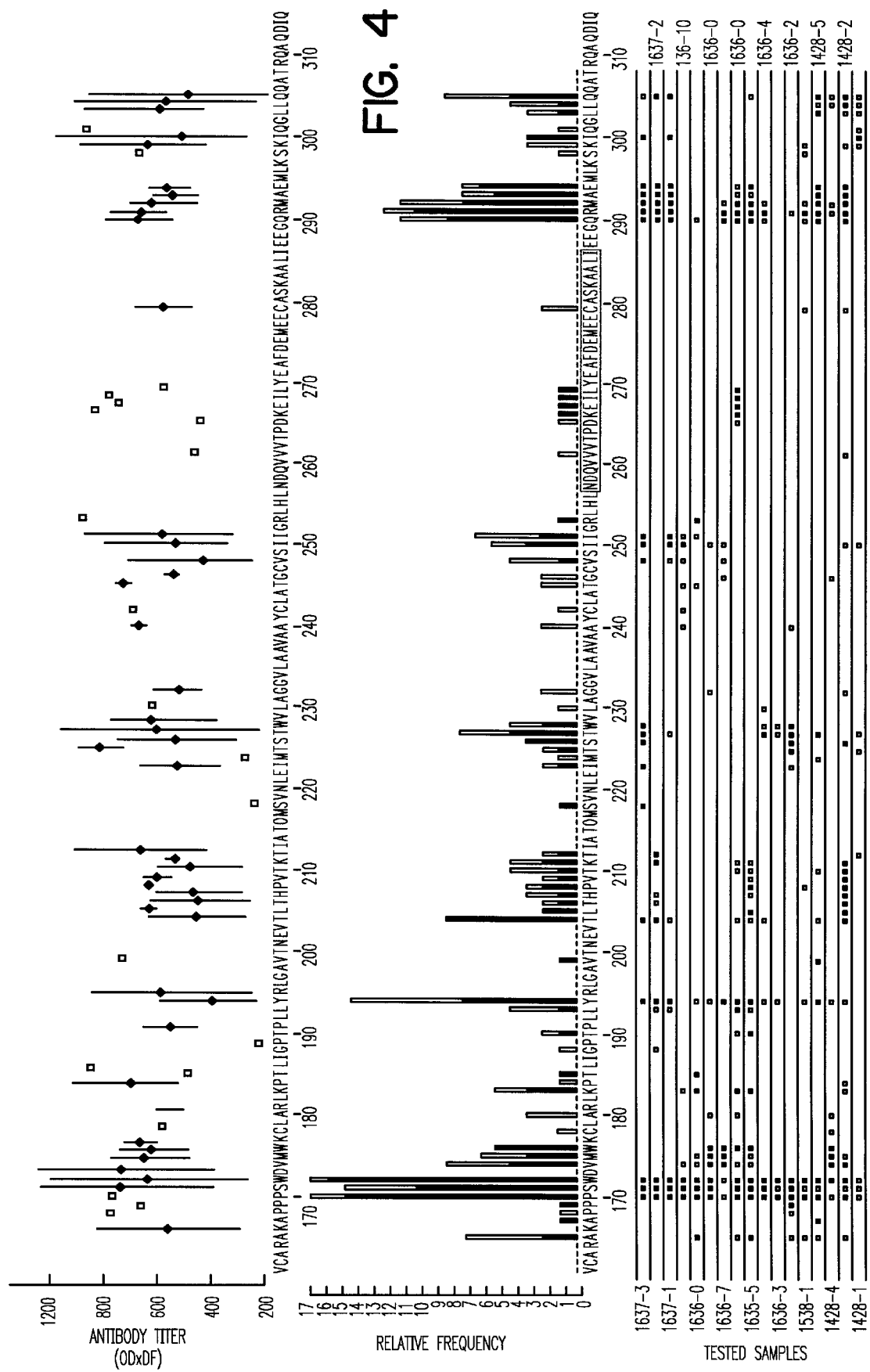
FIG. 4 (SEQ ID NO:2) is a compilation of graphs depicting the results of epitope mapping of HCV 2b (Nomoto).

"Hepatitis C virus" or "HCV" refers to the viral species of which pathogenic types cause NANBH, and attenuated types or defective interfering particles derived therefrom. See generally, publications cited in the section entitled "Background." The HCV genome is comprised of RNA. RNA containing viruses have relatively high rates of spontaneous mutation reportedly on the order of $10^{-3}$ to $10^{-4}$ per incorporated nucleotide. Fields & Knipe (1986) "Fundamental Virology" (Raven Press, N.Y.). Since heterogeneity and fluidity of genotype are inherent in RNA viruses, there are multiple types/subtypes, within the HCV species which may be virulent or avirulent. The propagation, identification, detection, and isolation of various HCV types or isolates is documented in the literature. As depicted herein, all nucleotide and amino acid residue sequences are from the HCV types noted. The number of the HCV-1 genome and amino acid residues sequences is as described in Choo et al. (1990) Brit. Med. Bull., 46:423–441. The disclosure herein allows the diagnosis of the various types.

As used herein, "type" refers to HCVs that differ genotypically by more than about 30%; "subtype" refers to HCVs that differ genotypically by about 10–20% and "isolate" refers to HCVs that differ genotypically by about less than 10%. "Typing" refers to distinguishing one type of HCV from another type.

Information on several different HCV types/subtypes is disclosed in International Publication No. WO 93/00365 particularly type or subtype CDC/HCV1 (also called HCV-1). Information from one type or subtype, such as a partial genomic or amino acid sequence, is sufficient to allow those skilled in the art using standard techniques to isolate new types of HCV. For example, several different types of HCV were screened as described below. These types, which were obtained from a number of human seral(and from different geographical areas), were typed utilizing the method and reagents described herein.

The genomic structure and the nucleotide sequence of HCV-1 genomic RNA has been deduced. The genome appears to be single-stranded RNA containing 10,000 nucleotides. The genome is positive-stranded, and possesses a continuous, translational open reading frame (ORF) that encodes a polyprotein of about 3,000 amino acids. In the ORF, the structural protein(s) appear to be encoded in approximately the first quarter of the amino-terminus, region, with the majority of the polyprotein responsible for non-structural (NS) proteins. When compared with all known viral sequences, small but significant co-linear homologies are observed with the non-structural (NS) proteins of the flavivirus family, and with the pestivirluses (which are now also considered to be part of the Flavivirus family).

Based upon the putative amino acid residues encoded in the nucleotide sequence of HCV-1 and other evidence, possible protein domains of the encoded HCV polyprotein, as well as the approximate boundaries, are presented in Table 1.

TABLE 1

| Putative Domain | Approximate Boundary (amino acid nos.) |
|---|---|
| C(nucleocapsid protein) | 1–191 |
| E$_1$ (virion envelope protein) | 192–383 |
| E$_2$/NS1 (envelope?) | 384–800 |
| NS2 (unknown function) | 800–1050 |
| NS3 (protease?) | 1050–1650 |
| NS4 (unknown function) | 1651–2100 |
| NS5 (polymerase) | 2100–3011(end) |

These domains are tentative. For example, the E2/NS1–NS2 border is probably in the 750–810 region, and NS3–NS4 border is about 1640–1650. There is also evidence that the 191 amino acid (aa) version of C is a precursor that is further processed to about 170 aa in length, and that the NS2, NS4 and NSS proteins are each further processed into two mature proteins.

Different types of HCV are defined according to various criteria such as, for example, an ORF of approximately 9,000 nucleotides to approximately 12,000 nucleotides, encoding a polyprotein similar in size to that of HCV-1, an encoded polyprotein of similar hydrophobic and/or antigenic character to that of HCV-1, and the presence of co-linear polypeptide sequences that are conserved with HCV-1.

The following parameters of nucleic acid homology and amino acid homology are applicable, either alone or in combination, in identifying HCV types. Generally, as described above, different types of HCV are about 70% homologous whereas subtypes are about 80–90% homologous and isolates are about 90% homologous.

As used herein, a polynucleotide "derived from" a designated sequence refers to a polynucleotide sequence which is comprised of a sequence of at least about 6 nucleotides, preferably at least about 8 nucleotides, more preferably. at least about 10–12 nucleotides, and even more preferably at least about 15–20 nucleotides corresponding to a region of the designated nucleotide sequence. "Corresponding" means homologous to or complementary to the designated sequence. Preferably, the sequence of the region from which the polynucleotide is derived is homologous to or complementary to a sequence which is unique to an HCV genome. Hybridization techniques for determining the complementarity of nucleic acid sequences are known in the art. See, for example, Maniatis et al. (1982). In addition, mismatches of duplex polynucleotides formed by hybridization can be determined by known techniques, including for example, digestion with a nuclease such as Si that specifically digests single-stranded areas in duplex polynucleotides. Regions from which typical DNA sequences may be "derived" include but are not limited to, for example, regions encoding type specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

Similarly, a polypeptide or amino acid sequence "derived from" a designated amino acid or nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence. This terminology also includes a polypeptide expressed from a designated nucleic acid sequence.

A recombinant or derived polypeptide is not necessarily translated from a designated nucleic acid sequence; it may be generated in any manner, including for example, chemical synthesis, or expression of a recombinant expression system, or isolation from HCV, including mutated HCV. The polypeptides described herein are generally relatively short and are thus most easily chemically synthesized.

A recombinant or derived polypeptide may include one or more analogs of amino acids or unnatural amino acids in its sequence. Methods of inserting analogs of amino acids into a sequence are known in the art. It also may include one or more labels, which are known to those of skill in the art. A detailed description of analogs and "mimotopes" is found in commonly owned, co-pending U.S. patent application Ser. No. 07/972,755.

Peptide analogs include deletions, additions, substitutions or modifications thereof which retain the HCV typing capability. Preferred "substitutions" are those which are conservative, i.e., wherein a residue is replaced by another of the same general type. As is well understood, naturally-occurring amino acids can be subclassified as acidic, basic, neutral and polar, or neutral and nonpolar. Furthermore, three of the encoded amino acids are aromatic. It is generally preferred that encoded polypeptides differing from the natural epitope contain substituted codons for amino acids which are from the same group as that of the amino acid replaced. Thus, in general, the basic amino acids Lys, Arg, and His are interchangeable; the acidic amino acids aspartic and glutamic are interchangeable; the neutral polar amino acids Ser, Thr, Cys, Gln, and Asn are interchangeable; the nonpolar aliphatic amino acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable. While proline is a nonpolar neutral amino acid, it represents difficulties because of its effects on conformation, and substitutions by or for proline are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids.

It should further be noted that if the polypeptides are made synthetically, substitutions by amino acids which are not encoded by the gene may also be made. Alternative residues include, for example, the omega amino acids of ,the formula $H_2N(CH_2)_nCOOH$ wherein n is 2–6. These are neutral, nonpolar amino acids, as are sarcosine (Sar), t-buityi alanine (t-BuA), t-butyl glycine (t-BuG), N-methyl Ile. (N-MeIle), and norleucine (Nle). Phenyl glycine, for example, can be substituted for Trp, Tyr or Phe an aromatibc neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be retained if one or more of these is substituted by hydroxyproline (Hyp).

The term "recombinant polynucleotide" as used herein intends a polynucleotide of genomic, cDNA, semisynthetic, or synlthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also incudes known types of modifications, for example, labels which are known in the art, methylation, "caps", substitution of one or more naturally occurring nucleotides with an analog, internucleotide modifications such as, for example, those with uncharged linkages (e.g., methyl phosphonates, phosphotriesters, phdsphoramidates, carbamates, etc.) and with charged linkages (e.g., phosphorothioates, phosphorodithioates, etc.), those containing pendant moieties, such as, for example proteins including but not limited to nucleases, toxins, antibodies, signal peptides and poly-L-lysine; those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. The polynucleotides described herein are relatively short and are thus most easily chemically synthesized.

A "purified" polypeptide refers to the polypeptide being in a state that is substantially free of other polypeptides, i.e., in a composition that contains a minimum of about 50% by weight (desired polypeptide/total polypeptide in composition), preferably a minimum of about 70%, and even more preferably a minimum of about 90% of the desired polypeptide, without regard to nonproteinaceous materials in the composition. Techniques for purifying viral polypeptides are known in the art. Purified antibodies are similarly defined in the art.

As used herein, "epitope" refers to an antigenic determinant of a polypeptide. An epitope could comprise 3 or more amino acids that define the binding site of an antibody. Generally an epitope consists of at least 5 amino acids, and sometimes consists of at least 8 amino acids. Methods of epitope mapping are known in the art.

As used herein, "type specific epitope" refers to an epitope that is found on one HCV type. A "type-cluster specific epitope" is found on more than one but fewer than all HCV types. For instance, a particular epitope may be recognized by antibodies from a patient infected with HCV 1 but not recognized by or recognized less efficiently by antibodies from a patient infected with HCV 2. Similarly, a type-cluster specific epitope derived from HCV-3 may be recognized by antibodies from a patient infected with HCV-3 or HCV-4 but not by antibodies from a patient infected with HCV-1 or HCV-2. "Conserved epitopes" are those which are recognized by antibodies specific to all HCV types.

A polypeptide is "immunologically reactive" with an antibody which binds to the peptide due to antibody recognition of a specific epitope contained within the polypeptide. Immunological reactivity may be determined by antibody binding, more particularly by the kinetics of antibody binding, and/or by competition in binding using as competitors known polypeptides containing an epitope against which the antibody is directed. The techniques for determining whether a polypeptide is immunologically reactive with an antibody are known in the art.

As used herein, the term "antibody" refers to a polypeptide or group of polypeptides which are comprised of at least one antibody combining site. An "antibody combining site" or "binding domain" is formed from the folding of variable domains of an antibody molecule(s) to form three-dimensional binding spaces with an internal surface shape and charge distribution complementary to the features of an epitope of an antigen, which allows an immunological reaction with the antigen. An antibody combining site may be formed from a heavy and/or a light chain domain ($V_H$ and $V_L$, respectively), which form hypervariable loops which contribute to antigen binding. The term "antibody" includes, for example, vertebrate antibodies, hybrid antibodies, chimeric antibodies, altered antibodies, univalent antibodies, the Fab proteins, and single domain antibodies.

Antibodies specific to polypeptides can be made by any method known in the art. For instance, the polypeptides are generally suspended in a physiologically acceptable buffer, mixed with a suitable adjuvant and injected into an animal. Methods of making polyclonal and monoclonal antibodies are known in the art and will not be described in detail herein.

The term "polypeptide" refers to a polymer of amino acids and does not refer to a specific length of the product; thus, polypeptides, oligopeptides, and proteins are included within the definition of polypeptide. This term also does not refer to or exclude post-expression modifications of the polypeptide, for example, glycosylation, acetylation, phosphorylation, and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Treatment", as used herein, refers to prophylaxis and/or therapy.

An "individual", as used herein, refers to vertebrates, particularly members of the mammalian species, and includes, but is not limited to, animals (e.g., dogs, cats, cattle, swine, sheep, goat, rabbits, mice, rats, guinea pigs, etc.), and primates, including monkeys, chimps, baboons and humans.

As used herein, the "sense strand" of a nucleic acid contains the sequence that has sequence homology to that of mRNA. The "anti-sense strand" contains a sequence which is complementary to that of the "sense strand".

As used herein, a "positive stranded genome" of a virus is one in which the genome, whether RNA or DNA, is single-stranded and which encodes a viral polypeptide(s). Examples of positive stranded RNA viruses include Togaviridae, Coronaviridae, Retroviridae, Picornaviridae, and Caliciviridae. Included also, are the Flavivirus, which were formerly classified as Togaviradae. See Fields & Knipe (1986).

As used herein, "antibody containing body sample" refers to a component of an individual's body which is a source of the antibodies of interest. Antibody containing body components are known in the art, and include but are not limited to, for example, plasma, serum, spinal fluid, lymph fluid, the external sections of the respiratory, intestinal, and genitourinary tracts, tears, saliva, milk, white blood cells, and myelomas.

As used herein, a "biological sample" refers to a sample of tissue or fluid isolated from an individual, including, but not limited to, for example, plasma, serum, spinal fluid, lymph fluid, the external sections of the skin, respiratory, intestinal and genitourinary tracts, tears, saliva, milk, blood cells, tumors, organs. Also included are samples of in vitro cell culture constituents (including, but not limited to, conditioned medium resulting from the growth of cells in culture medium, putatively virally infected cells, recombinant cells, and cell components).

DESCRIPTION OF THE INVENTION

The practice of the present invention will employ, unless otherwise indicated, conventional techniques of molecular biology, microbiology, recombinant DNA, polypeptide and nucleic acid synthesis, and immunology, which are within the skill of the art. Such techniques are explained fully in the literature. See, e.g., Maniatis, Fitsch & Sambrook, "Molecular Cloning: A Laboratory Manual" (1982); "DNA Cloning, Volumes I and II" (D. N. Glover ed. 1985); "Oligonucleotide Synthesis" (M. J. Gait ed., 1984); "Nuclei Acid Hybridization" (B. D. Hames & S. J. Higgins eds. 1984); "Transcription and Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984); the series, "Methods in Enzymology" (Academic Press, Inc.); "Gene Transfer Vectors For Mammalian Cells" (J. H. Miller and M. P. Calos eds., 1987, Cold Spring Harbor Laboratory), Meth. Enzymol., Vol. 154 and Vol. 155 (Wu and Grossman, and Wu, eds., respectively), Mayer and Walker, eds. (1987), "Immunochemical Methods In Cell And Molecular Biology" (Academic Press, London); Scopes, (1987) "Protein Purification: Principles and Practice", Second Edition (Springer-Verlag, N.Y.); and "Handbook of Experimental Immunology", Volumes I–IV (D. M. Weir and C. C. Blackwell eds. 1986).

All patents, patent applications and publications mentioned herein, both supra and infra, are hereby incorporated herein by reference.

The invention includes methods for detecting HCV and identifying infection by different types of HCV. The invention also includes polypeptides and nucleic acid molecules for use in the methods.

The methods for detecting and typing infection by HCV include both immunoassays and nucleic acid identification by methods including, but not limited to, Southern blot analysis and polymerase chain reaction. In order to identify infection by HCV, a biological sample is incubated with one of the polypeptides described herein under conditions which permit antigen-antibody binding and a determination is made as to whether antibodies in the sample bind to the epitope found on the polypeptide.

Immunoassay and Diagnostic Kits

The polypeptides containing the type specific epitopes and type-cluster specific epitopes are useful in immunoassays to detect the presence of HCV antibodies, or the presence of the virus and/or viral antigens, in biological samples. Design of the immunoassays is subject to a great deal of variation, and many formats are known in the art. The immunoassay will utilize at least one type specific epitope or type-cluster specific epitope. In one embodiment, the immunoassay uses a combination of type specific epitopes and/or type-cluster specific epitopes.

The polypeptides are useful for typing HCV by using the epitopes to determine the presence of type specific or type-cluster specific antibodies. The polypeptides are also suitable for use in generating type specific or type-cluslter specific antibodies that can then be used in an immunoassay to distinguish between various types of HCV.

The polypeptides are derived from three different regions of the HCV genome. One set of polypeptides includes a type or type cluster specific epitope obtained from. the HCV core region. Another set of polypeptides includes a type or type cluster specific epitope obtained from the HCV non-structural region 4 (NS4). Another set of polypeptides includes a type or type-cluster specific epitope obtained from the non-structural region 5 (NS5) of a hepatitis C virus. This set is found between amino acid residues 2281–2313 of HCV-1 and homologouslregions of other types of hepatitis C virus.

The polypeptides are suitable for use in immunoassays for one or more HCV types. In order to assay for one type the sample is contacted with one or more polypeptides containing a type-cluster specific epitope under conditions which permit antigen-antibody binding and determining whether antibodies in the sample bind to the epitope.

In an immunoassay to distinguish a particular type of HCV, a biological sample is obtained from an individual, contacted with a first type specific epitope or type-cluster specific epitope under conditions which permit antigen-antibody binding; contacted with a second type specific epitope or type-cluster specific epitope under conditions which permit antigen-antibody binding and determining whether antibodies in the sample bind to either the first or second epitope. These steps can be repeated with any number of polypeptides containing type and/or type-cluster specific epitopes.

Typically, an immunoassay for anti-HCV antibody(s) involves 'selecting and preparing the test sample suspected of containing the antibodies, such as a biological sample, then incubating it with the type specific epitope or type-cluster specific epitope under conditions that allow antigen-antibody complexes to form, and then detecting the formation of such complexes. Suitable incubation conditions are well known in the art. The immunoassay may be, without limitations, in a heterogeneous or in a homogeneous format, and of a standard or competitive type.

In a heterogeneous format, the type specific epitope or type-cluster specific epitope is typically bound to a solid support to facilitate separation of the sample from the polypeptide after incubation. Examples of solid supports that can be used include, but are not limited to, nitrocellulose (e.g., in membrane or microtiter well form), polyvinyl chloride (e.g., in sheets or microtiter wells), polystyrene latex (e.g., in beads or microtiter plates), polyvinylidine fluoride (known as Immulon®), idiazotized paper, nylon membranes, activated beads, and Protein A beads. For example, Dynatech Immulon® 1 or Immulon® 2 microtiter plates or 0.25 inch polystyrene beads (Precision Plastic Ball) can be used in the heterogeneous format. The solid support containing the type specific epitope or type-cluster epitope is typically washed after separating it from the test sample, and prior to detection of bound antibodies. Both standard and competitive formats are known in the art.

In a homogeneous format, the test sample is incubated with the type specific epitope or type cluster epitope in solution. For example, it may be under conditions that will precipitate any antigen-antibody complexes which are formed. Both standard and competitive formats for these assays are known in the art.

In a standard format, the amount of HCV antibodies forming the antibody-type or type-cluster specific epitope complex is directly monitored. This may be accomplished by determining whether labeled anti-xenogeneic (e.g., anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

In an inhibition assay, the ability of antibodies to bind to polypeptides containing various different type specific epitopes or type-cluster specific epitopes is determined. The antibodies are first exposed to polypeptides containing epitope(s) from one type or type-cluster of HCV and then to polypeptides containing epitope(s) from another type or type-cluster of HCV. The process may be repeated for additional types of HCV.

Complexes formed comprising anti-HCV antibody (or, in the case of competitive assays, the amount of competing antibody) are detected by any of a number of known techniques, depending on the format. For example, unlabeled HCV antibodies in the complex may be detected using a conjugate of antixenogeneic Ig complexed with a label, (e.g., an enzyme label).

In typical immunoassays, the test sample, typically a biological sample, is incubated with polypeptides containing one or more type specific epitopes or type-cluster specific epitopes under conditions that allow the formation of antigen-antibody complexes. Various formats can be employed. For example, a "sandwich assay" may be employed, where antibody bound to a solid support is incubated with the test sample; washed; incubated with a second, labeled antibody to the analyte, and the support is washed again. Analyte is detected by determining if the second antibody is bound to the support. In a competitive format, which can be either heterogeneous or homogeneous, a test sample is usually incubated with antibody and a labeled, competing antigen is also incubated, either sequentially or simultaneously. These and other formats are well known in the art.

Antibodies directed against the type specific epitopes or type-cluster specific epitopes can be used in immunoassays for the detection of viral antigens in patients with HCV caused NANBH, and in infectious blood donors. Moreover, these antibodies may be extremely useful in detecting acute-phase donors and patients.

An immunoassay may use, for example, a monoclonal antibody directed towards a type specific epitope or type-cluster specific epitopes, a combination of monoclonal antibodies directed towards epitopes of one viral antigen, monoclonal antibodies directed towards epitopes of different viral antigens, polyclonal antibodies directed towards the same viral antigen, or polyclonal antibodies directed towards different viral antigens. Protocols may be based, for example, upon competition, or direct reaction, or sandwich type assays. Protocols may also, for example, use solid supports, or may be by immunoprecipitation. Most assays involve the use of labeled antibody or polypeptide; the labels may be, but are not limited to, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

The invention further includes nucleic acid molecules encoding the amino acid residue sequences of the type specific epitopes and type-cluster specific epitopes described. These nucleic acid molecules are useful as probes for instance in Southern blots or other DNA recognition assays such as the capture assay described in U.S. Pat. Nos. 4,868,105 and 5,124,246.

The studies on antigenic mapping by expression of HCV cDNAs showed that a number of clones containing these cDNAS expressed polypeptides which were immunologically reactive with serum from individuals exhibiting NANBH. No single polypeptide was immunologically reactive with all sera. Five of these polypeptides were very immunogenic in that antibodies to the HCV epitopes in these polypeptides were detected in many different patient sera, although the overlap in detection was not complete. Thus, the results on the immunogenicity of the polypeptides encoded in the various clones suggest that efficient detection systems for HCV infection may include the use of panels of epitopes. The epitopes in the panel may be constructed into one or multiple polypeptides. The assays for the varying epitopes may be sequential or simultaneous.

Kits suitable for immunodiagnosis and containing the appropriate labeled reagents are constructed by packaging the appropriate materials, including the polypeptides of the invention containing type specific epitopes and type-cluster epitopes or antibodies directed against type specific epitopes and type-cluster specific epitopes in suitable containers, along with the remaining reagents and materials required for the conduct of the assay, as well as a suitable set of assay instructions.

The invention further includes nucleic acid molecules complementary to the nucleic acid sequences flanking regions encoding the type specific epitopes and type-cluster specific epitopes. Such nucleic acid molecules are useful in performing PCR to determine the genotype of a particular HCV.

It should be noted that there are variable and hypervariable regions: within the HCV genome; therefore, the homology in these,regions is expected to be significantly less than that in the overall genome.

The techniques for determining nucleic acid and amino acid sequence homology are known in the art. For example, the amino acid sequence may be determined directly and compared to the sequences provided herein. Alternatively the nucleotide sequence of the genomic material of the putative HCV may be determined (usually via a cDNA intermediate), the amino acid sequence encoded therein can be determined, and the corresponding regions compared.

The foregoing discussion and examples only illustrate the invention, persons of ordinary skill in the art will appreciate that the invention can be implemented in other ways, and the invention is defined solely by reference to the claims.

EXAMPLE 1

Comparison of Mayor Epitopes of Various Different Types of HCV

The amino acid residue homology between different types and subtypes of HCV was compared for various regions. The. subtype of HCV is as described by Simmonds phylogenetic analysis. The amino acid sequence numbering corresponds to that described for the prototype HCV-1 sequence. Choo et al. (1989) Table 2 shows the percent amino acid residue homology for NS4 region type specific epitopes and type-cluster specific epitopes and the conserved major epitope. Table 3 shows the amino acid residue homology between two type specific epitopes or type-cluster specific of the NS5 region. Table 4 shows the percent amino acid residue homology for core region conserved major epitopes and type specific epitopes.

TABLE 2

Amino Acid Homologies (%) Between Different HCV Subtypes

| HCV subtype | Example types abbreviation | NS4 region type specific major epitopes (1689–1718 aa)* | NS4 region conserved major epitope (1910–1936 aa)* |
| --- | --- | --- | --- |
| 1a | HCV-1 (1a) vs (1a) | 100% | 100% |
| 1b | HCV-J (1a) vs (1b) | 83% | 100% |
| 2a | HCV-J6 (1a) vs (2a) | 47% | 93% |
| 2b | HCV-J8 (1a) vs (2b) | 43% | 93% |

TABLE 3

Amino Acid Homologies (%) Between Different HCV Subtypes

| HCV subtype | Example types abbreviation | NS5 region type specific major epitopes (2281–2313 aa)* | NS5 region type specific major epitope (2673–2707 aa)* |
| --- | --- | --- | --- |
| 1a | HCV-1 (1a) vs (1a) | 100% | 100% |
| 1b | HCV-J (1a) vs (1b) | 76% | 89% |
| 2a | HCV-J6 (1a) vs (2a) | 70% | 83% |
| 2b | HCV-J8 (1a) vs (2b) | 73% | 83% |
| 3a | HCV-E-b1 (1a) vs (3a) | | 77% |
| 3b | HCV-Tb (1a) vs (3b) | | 83% |

TABLE 4

Amino Acid Residue Homology (%) Between Different HCV Subtypes

| HCV subtype | Example types abbreviation | Core region conserved major epitopes (10–45 aa)* | Core region type specific major epitopes (67–84 aa)* |
| --- | --- | --- | --- |
| 1a | HCV-1 (1a) vs (1a) | 100% | 100% |
| 1b | HCV-J (1a) vs (1b) | 98% | 100% |
| 2a | HCV-J6 (1a) vs (2a) | 98% | 61% |
| 2b | HCV-J8 (1a) vs (2b) | 98% | 61% |
| 3a | HCV-E-b1 (1a) vs (3a) | 93% | 89% |
| 4 | HCV-EG-21 (1a) vs (4) | 98% | 83% |

EXAMPLE 2

Peptide Synthesis

Two sets of polypeptides were synthesized. The first set was designed to perform epitope mapping of HCV-1 and the second set was designed to determine which epitopes identified in the epitope mapping studies contained type specific epitopes. In the first set of polypeptides, sixty-four sets (in duplicate) of overlapping octapeptides were synthesized by Mimotopes across the entire HCV-1 polyprotein (3011 amino acid residues).

The second set of polypeptides were made according to the method described by Geysen (1990) *J. Trop. Med. Pub. Health*, 21:523–533; and Merrifield (1963) *J. Am. Chem. Soc.*, 85:2149–2154.

In the second set of polypeptides, four antigenic regions which represent the major epitopes of non-conservative sequences in HCV-1 from core, NS4, NS5 and their corresponding sequences from HCV subtypes 1b, 2a, 3a and type 4 were selected for type specific epitope synthesis. The sequence from core was selected from the less conserved region of amino acid residues 67–84. The sequence from the NS4 region was selected from the amino acid residue region 1689–1718. The sequences selected from the NS5 region were from the amino acid residue regions 2281–2313 and, 2673–2707.

EXAMPLE 3

Biological Samples

In order to determine the effectiveness of the polypeptides in distinguishing between antibodies specific to different types of HCV, antisera were obtained from twenty-four chronic NANBH patients from different areas of the world including the United States east coast and west coast, Japan, western European countries, southern European countries and South Africa. The viral RNA isolation, cDNA synthesis, PCR amplification, DNA sequencing and oligonucleotide probe hybridization were performed as described by Cha et al. (1992) *Proc. Natl. Acad. Sci. USA*, 89:7144–7148.

EXAMPLE 4

Epitope Mapping Procedures

In order to determine which regions of HCV contain epitopes, whether group specific or conserved, the entire HCV-1 polyprotein was subject to epitope mapping. The method used is essentially as outlined in FIG. 2.

Sixty-four sets (in duplicate) of overlapping octapeptides were synthesized by Mimotopes across the entire HCV-1 polyprotein (3011 amino acids). A panel of 40 samples which contain 25 United States HCV antibody reactive samples, 9 Japan HCV reactive samples and 6 HCV non-reactive negative control samples were selected for epitope mapping and cluster analysis. The immunoassays were performed using standard ELISA procedures.

The criteria for identifying the major epitopes were based on the antibody reaction frequency and the antibody reaction intensity (titer) to these epitopes. The results are presented in FIGS. 3 and 4 (SEQ ID NO:1 and SEQ ID NO:2).

EXAMPLE 5

Polypeptide Derived Enzyme-linked Immunosorbent Assays

In order to determine the optimal immunoassay utilizing the polypeptides described in Example 2, two separate types of polypeptide derived enzyme-linked immunosorbent assay (ELISA) were run and the results were compared. The first type of ELISA was the Nunc MaxiSorb™ on which the polypeptides are simply adsorbed and the second type utilized Nunc Covalink NH™ on which the polypeptides are covalently linked. Formation of amide bonds between carboxylic acids and amines is initiated by the addition of carbodiimide. To reduce hydrolysis, the active ester can be made by adding N-hydroxy-succinimide (NHS) to the above conjugation procedures.

The microtiter plates for the first type of ELISA was performed as follows. The polypeptides were placed in the wells of the Nunc MaxiSorb™ microtiter plates at a concentration of 1 μg/well in 100 μl of phosphate buffered saline (PBS). The polypeptides were allowed to absorb overnight at room temperature. The microtiter plates were then washed four times with PBS without detergent. The wells were then post-coated with 220 μl Superblock® (Pierce) for one hour and then aspirated without further washing and vacuum dried.

The assay was performed as follows. The sera sample size of 5 μl was added to the wells with 100 μl of 5% nonfat milk and incubated for one hour at 37° C. The wells were then washed five times in PBS with 0.05% Tween. A conjugate of affinity purified goat anti-human IgG labeled with horse radish peroxidase (Jackson Laboratories) was then used to determine the degree of binding of human antibodies to the polypeptides. The conjugate was previously diluted to 5% IgG in 150 mM NaCl, PBS, 5% horse serum (heat denatured). 100 μl of the conjugate was placed in the wells and incubated for one hour at 37° C. The wells were then washed five times with PBS/Tween and OPD [o-phenylene-diamine-2HCl, one tablet per developer buffer (citrate phosphate buffered 0.02% $H_2O_2$); Sigma] for thirty minutes at room temperature and the Abs at 492 nm and 620 nm were determined. The cut off was determined from 200 random (normal) samples where seven standard deviations from the mean or about 0.45.

The microtiter plates for the second type of ELISA was performed as follows. The polypeptides were placed in the wells of the Nunc MaxiSorb™ microtiter plates at a concentration of 10 mg/well in 50 μl of water. 25 μl of 0.1 M NHS (sulfo-N-hydrosuccinimide, Pierce) and 25 μl of 0.1 M EDC [1-Ethyl-3(3-dimethylaminopropylcarbodiimide) Sigma] were added to the polypeptides and mixed at room temperature for 30 minutes on a rocking platform. The entire contents were then added to 52 ml of ice cold 0.1 M Na Carbonate pH 8.6. 100 μl of the mixture was used to coat the wells of the microtiter plates and then incubated at 4° C. for 30 minutes. The plates were then washed four times with PBS/0.1% Triton X-100. The plates were then treated with Superblock® and the assay was performed as described above.

The results obtained are presented in the following Tables.

TABLE 5

Serotyping Epitope Analysis from Different HCV Types

| Sequence Region: | NS4 (1689–1718) | | |
|---|---|---|---|
| Sample ID | Peptide EIA | Peptide (HCV Type) | Type dependent sequences |
| (I) Paid Donor Samples | | | SGKPAIIPDREVLYREFDEMEECSQHLPYI (SEQ ID NO:17) |
| | | cp402-10 (1a) | SGKPAIIPDREVLYREFDEMEECSQHLPYI (SEQ ID NO:17) |
| | | cp402-11 (1b) | SGRPAVIPDREVLYQFDEMEECASHLPYI (SEQ ID NO:18) |
| | | cp402-12 (2a) | NQRAVVAPDKEVLYEAFDEMEECASRAALI (SEQ ID NO:19) |
| | | cp402-13 (2b) | NDRVVVAPDKEILYEAFDEMEECASKAALI (SEQ ID NO:20) |
| | | | \* \*   \*     \* |
| Paid Donor Samples LL57406 | 4.23 | cp402-10 (1a) | |
| | 6.48 | cp402-11 (1b) | |
| | 6.84 | cp402-12 (2a) | |
| | 3.41 | cp402-13 (2b) | |
| | 6.57 | sodC100 ELISA (1a) | |
| React with common epitopes 1a, 1b, 2a & 2b | | | PDREVLY / K I  (SEQ ID NO:21) |
| (II) Sample react with type-specific epitopes 84-018669 | 3.76 | cp402-10 (1a) | |
| | 7.88 | cp402-11 (1b) | |
| | 6.20 | cp402-12 (2a) | |
| | 8.94 | cp402-13 (2b) | |
| | 6.45 | sodC100 ELISA (1a) | |
| React with common epitope for 1a, 1b, 2a & 2b | | | PDREVLY / K I  (SEQ ID NO:21) |

TABLE 6

Serotyping Epitope Analysis from Different HCV Types

Sequence Region: NS4 (1689–1718)

| Sample ID | Peptide EIA | Peptide (HCV Type) | Type dependent sequences |
|---|---|---|---|
| (I) Paid Donor Samples | | | SGKPAIIPDREVLYREFDEMEECSQHLPYI (SEQ ID NO:17) |
| | | cp402-10 (1a) | SGKPAIIPDREVLYREFDEMEECSQHLPYI (SEQ ID NO:17) |
| | | cp402-11 (1b) | SGRPAVIPDREVLYQFDEMEECASHLPYI (SEQ ID NO:18) |
| | | cp402-12 (2a) | NQRAVVAPDKEVLYEAFDEMEECASRAALI (SEQ ID NO:19) |
| | | cp402-13 (2b) | NDRVVVAPDKEILYEAFDEMEECASKAALI (SEQ ID NO:20) |
| | | | * *       *        * |
| Paid Donor Samples LL57406 | 4.23 | cp402-10 (1a) | |
| | 6.48 | cp402-11 (1b) | |
| | 6.84 | cp402-12 (2a) | |
| | 3.41 | cp402-13 (2b) | |
| | 6.57 | sodC100 ELISA (1a) | |
| React with common epitopes 1a, 1b, 2a & 2b | | | PDREVLY / K I (SEQ ID NO:21) |
| (II) Sample react with type-specific epitopes 84-018669 | 3.76 | cp402-10 (1a) | |
| | 7.88 | cp402-11 (1b) | |
| | 6.20 | cp402-12 (2a) | |
| | 8.94 | cp402-13 (2b) | |
| | 6.45 | sodC100 ELISA (1a) | |
| React with common epitope for 1a, 1b, 2a & 2b | | | PDREVLY / K I (SEQ ID NO:21) |

TABLE 7

Serotyping Epitope Analysis from Different HCV Types

Sequence Region: NS4 (1689–1718)

| Sample Description | Peptide EIA Signal/Cutoff | Peptides from different HCV types | Type dependent sequences | |
|---|---|---|---|---|
| (I) Paid Donor Samples | | | SGKPAIIPDREVLYREFDEMEECSQHLPYI (SEQ ID NO:17) | |
| | | cp402-10 (1a) | SGKPAIIPDREVLYREFDEMEECSQHLPYI (SEQ ID NO:18) | |
| | | cp402-11 (1b) | SGRPAVIPDREVLYQEFDEMEECASHLPYI (SEQ ID NO:19) | |
| | | cp402-12 (2a) | NQRAVVAPDKEVLYEAFDEMEECASRAALI (SEQ ID NO:20) | |
| | | cp402-13 (2b) | NDRVVVAPDKEILYEAFDEMEECASKAALI (SEQ ID NO:22) | |
| | | | * *       *        * | |
| MT-32 (2a & 2b) | 0.68 | cp402-10 (1a) | | |
| | 0.67 | cp402-11 (1b) | | |
| | 7.81 | cp402-12 (2a) | Reactive with type specific epitope → | CASRAAL (SEQ ID NO:22) |
| | 6.88 | cp402-13 (2b) | | CASKAAL (SEQ ID NO:23) |
| | | | | * |
| | 0.23 | sodC100 ELISA (1a) | | |
| MT-79 (2a, 2b) | 0.27 | cp402-10 (1a) | | |
| | 0.34 | cp402-11 (1b) | | |
| | 5.53 | cp402-12 (2a) | Reactive with type specific epitope → | CASRAAL (SEQ ID NO:22) |
| | 4.72 | cp402-13 (2b) | | CASKAAL (SEQ ID NO:23) |
| | 0.41 | sodC100 ELISA (1a) | | |

TABLE 8

Serotyping Epitope Analysis from Different HCV Types

Sequence Region: NS5 (2673–2707)

| Sample Description | | Peptides from different HCV types | Type dependent sequences |
|---|---|---|---|
| (I) Chronic NANBH from Paid Donors | | | |
| | Peptide EIA S/CO | | |
| (1) 84-018433 (2b) | 3.39 | cp402-4 (1a) | IKSLTERLYVGGPLTNSRGENCGYRRCRASGVLTT (SEQ ID NO:24) |
| | 4.75 | cp402-5 (1b) | IRSLTERLYIGGPLTNSKGQNCGYRRCRASGVLTT (SEQ ID NO:25) |
| | 4.62 | cp402-6 (2a) | IHSLTERLYVGGPMFNSKGQTCGYRRCRASGVLTT (SEQ ID NO:26) |
| | 3.56 | cp402-9 (3b) | ISSLTERLYVGGPMFNSKGQSCGYRRCRASGVLTT (SEQ ID NO:27) |
| | 3.38 | cp402-7 (2b) | IHSLTERLYVGGPMTNSKGQSCGYRRCRASGVFTT (SEQ ID NO:28) |
| | 0.58 | cp402-8 (3a) | ISSLTERLYCGGPMFNSKGAQCGYRRCRASGVLPT (SEQ ID NO:29) |
| | 4.40 | r-NS5 ELISA | |
| Critical sequence change altered in the epitopes in this sample | | | <u>C</u>     <u>AQ</u>     P* |
| (2) FF25951 (1a) | 2.28 | cp402-4 (1a) | * |
| | 1.65 | cp402-5 (1b) | |
| | 1.28 | cp402-6 (2a) | |
| | 2.03 | cp402-9 (3b) | |
| | 1.47 | cp402-7 (2b) | |
| | 0.43 | cp402-8 (3a) | |
| | 4.81 | r-NS5 ELISA (1a) | |
| Critical sequence change altered in the epitope response in this sample | | | <u>C</u>     <u>AQ</u>     P*|

TABLE 9

Serotyping Epitope Analysis from Different HCV Types

Sequence Region: NS5 (2673–2707)

| Sample Description | | Peptides from different HCV types | Type dependent sequences |
|---|---|---|---|
| (I) Chronic NANBH from Paid Donors | | | |
| | Peptide EIA S/CO | | |
| (1) 84-018366 | 1.07 | cp402-4 (1a) | IKSLTERLYVGGPLTNSRGENCGYRRCRASGVLTT (SEQ ID NO:24) |
| | 1.01 | cp402-5 (1b) | IRSLTERLYIGGPLTNSKGQNCGYRRCRASGVLTT (SEQ ID NO:25) |
| | 1.52 | cp402-6 (2a) | IHSLTERLYVGGPMFNSKGQTCGYRRCRASGVLTT (SEQ ID NO:26) |
| | 1.16 | cp402-9 (3b) | ISSLTERLYVGGPMFNSKGQSCGYRRCRASGVLTT (SEQ ID NO:27) |
| | 0.58 | cp402-7 (2b) | IHSLTERLYVGGPMTNSKGQSCGYRRCRASGVFTT (SEQ ID NO:28) |
| | 0.48 | cp402-8 (3a) | ISSLTERLYCGGPMFNSKGAQCGYRRCRASGVLPT (SEQ ID NO:29) |
| | 1.68 | r-NS5 ELISA | |
| Critical sequence change altered in the epitopes in this sample | | | <u>C</u>     <u>AQ</u>     FP* |
| (2) 96727 | 3.80 | cp402-4 (1a) | |
| | 3.15 | cp402-5 (1b) | |
| | 2.52 | cp402-6 (2a) | |
| | 3.41 | cp402-9 (3b) | |
| | 0.79 | cp402-7 (2b) | |
| | 0.60 | cp402-8 (3a) | |
| | 5.54 | r-NS5 ELISA (1a) | |
| Critical sequence change altered in the epitope response in this sample | | | <u>C</u>     <u>AQ</u>     FP* |

TABLE 10

Summary of HCV Major type Specific Epitopes in Core, NS4 and NS5 Regions

```
Core Region:
Major Conserved Epitopes            type Specific Epitopes              Conserved Epitopes
(15—45)                             (67—84)                             (67—84)
TNRRPQDVKFPGGGQIVGGVY               HCV-1a & 1b-PEGRTWAQ(SEQ ID NO:31)  PGYPWP(SEQ ID NO:32)
LLPRRGPRLG (HCV-1)(SEQ ID NO:30)    HCV-2a & 2b-STGKSWGK(SEQ ID NO:33)
                                    HCV-3A or 4-SEGRSWAQ(SEQ ID NO:34)      F(4)

NS4 Region:
Major Conserved Epitopes            type Specific Epitopes              Conserved Epitopes
(1925—1935)                         (1689—1718)                         (1689—1718)
RGNHVSPTHYV (HCV-1)(SEQ ID NO:35)   HCV-1a-CSQHLPY(SEQ ID NO:36)        PDREVLY(SEQ ID NO:37)
                                    HCV-1b-CASHLPY(SEQ ID NO:38)        (1a, 1b)
                                    HCV-2a & 2b-CASRAAL(SEQ ID NO:39)      K I(2a, 2b)
                                                K NS5 Region:
Conserved Epitopes                  type Specific Epitopes
(2288—2294)                         (2281—2313)
WARPDYN(SEQ ID NO:40)               HCV-1a & 1b-PDYEPPVVHG(SEQ ID NO:41)
                                                   V
                                    HCV-2a-PDYQPATVAG(SEQ ID NO:42)
                                    HCV-2b-PGYEPPTVLG(SEQ ID NO:43)
                                    HCV-1a-FAQALPVW(SEQ ID NO;44)
                                    HCV-1b,2a&2b-FPPQALPIW(SEQ ID NO:45)
                                                  A
                                                  P Conserved Epitopes
(2673—2707)
RGENCGYRRCRASGVLTT-HCV-1a(SEQ ID NO:46)   KGAQCGYRRCRASGVLPT-HCV-3a(SEQ ID
 K QT(SEQ ID NO:47)HCV-1b, 2a               NO:49)
 K QS(SEQ ID NO:48)HCV-3b                        *
                                          KGQSCGYRRCRASGVFTT-HCV-2b(SEQ ID
                                            NO:50)
                                                 *
```

TABLE 11

Serotyping Epitope Analysis from Different Types of HCV Sequences (I) Chronic NANBH
from Paid Donors Sequence Region: Core (67–84)

| Sample ID | Peptide EIA S/CO | Peptide (HCV type) | Type Dependent Sequences |
|---|---|---|---|
| | | cp401-01 (1a&1b) | KARR PEGRTWAQ PGYPWP (SEQ ID NO:51) |
| | | cp401-02 (2A&2b) | KDRR STGKSWGK PGYPWP (SEQ ID NO:52) |
| | | cp401-04 (3a) | KARR SEGRSWAQ PGYPWP (SEQ ID NO:53) |
| | | cp401-05 (4) | KARR SEGRSWAQ PGFPWP (SEQ ID NO:54) |
| 84-017786 (1a) | 7.93 | cp401-01 (1a&1b) | |
| | 7.56 | cp401-02 (2A&2b)  Conserved epitope | PGYPWP (SEQ ID NO:32) |
| | 7.79 | cp401-04 (3a) | |
| | 6.86 | cp401-05 (4) | |
| | 6.61 | rC22 ELISA (2–120 aa) | |
| 84-018433 (2b) | 0.31 | cp401-01 (1a&1b) | PEGRTWAQ (SEQ ID NO:31) |
| | 7.52 | cp401-02 (2a&2b) | STGKSWGK (SEQ ID NO:55) Type specific epitopes |
| | 1.08 | cp401-04 (3a) | SEGRSWAQ (SEQ ID NO:34) |
| | 0.99 | cp401-05 (4) | SEGRSWAQ (SEQ ID NO:34) |
| | | | *    ** |
| 96696 (2b) | 6.18 | rC22 ELISA (2–120 aa) | |
| | 1.02 | cp401-01 (1a&1b) | PEGRTWAQ (SEQ ID NO:31) |
| | 4.75 | cp401-02 (2a&2b) | STGKSWGK (SEQ ID NO:55) |
| | 1.84 | cp401-04 (3a) | SEGRSWAQ (SEQ ID NO:34) |
| | 1.37 | cp401-05 (4) | SEGRSWAQ (SEQ ID NO:34) |
| | | | *    ** |
| | 6.23 | rC22 ELISA (2–120aa) | |

TABLE 12

Serotyping Epitope Analysis from Different Types of HCV Sequences (I) Chronic NANBH
from Paid Donors Sequence Region: NS5 (2281–2313)

| Sample ID (HCV Type) | Peptide EIA S/CO | Peptide | Type Dependent Sequences |
|---|---|---|---|
| | | | FAQALP VWARPDYNPPLVETWKKPDYEPPVVHG (SEQ ID NO:56) |
| | | | FPPALP IWARPDYNPPLLESWKDPDYVPPVVHG (SEQ ID NO:57) |
| | | | FPPALP AWARPDYNPPLVESWKRPDYQPATVAG (SEQ ID NO:58) |
| | | | FPPALP PWARPDYNPVLIETWKRPGYEPPTVLG (SEQ ID NO:59) |
| (1) 96690 (1a) | 4.59 | cp402-00 (1a) | FAQALPVW (SEQ ID NO:60) Type specific epitope |
| | 1.57 | cp402-01 (1b) | PP        I |
| | 1.16 | cp402-02 (2a) | PP        A |
| | 0.17 | cp402-03 (2b) | PP        P |
| | 5.64 | r-NS5ELISA (1a) | |
| (2) 84-01778 (2a) | 2.41 | cp402-00 (1a) | |
| | 0.47 | cp402-01 (1b) | |
| | 5.99 | cp402-02 (2a) | Type specific epitope PDYQPATVAG (SEQ ID NO:61) |
| | 0.42 | cp402-03 (2b) | |
| | 0.42 | r-NS5ELISA (1a) | |

TABLE 13

Serotyping Epitope Analysis from Different Types of HCV Sequences (I) Chronic NANBH
from Paid Donors Sequence Region: NS5 (2281–2313)

| Sample ID (HCV Type) | Peptide EIA S/CO | Peptide | Type Dependent Sequences |
|---|---|---|---|
| (1) NAC5 (1b) | 7.28 | cp402-00 (1a) | FAQALPV WARPDYN PPLVETWKK PDYEPPVVHG (SEQ ID NO:56) |
| | 6.59 | cp402-01 (1b) | FPPALPI WARPDYN PPLLESWKD PDYVPPVVHG (SEQ ID NO:57) |
| | 0.10 | cp402-02 (2a) | FPPALPA WARPDYN PPLLESWKR PDYQPATVAG (SEQ ID NO:62) |
| | 0.47 | cp402-03 (2b) | FPPALPP WARPDYN PVLIETWKR PGYEPPTVLG (SEQ ID NO:59) |
| | 6.36 | r-NS5ELISA | PDYEPPVVHG (1a) (SEQ ID NO:63) |
| | | | PDYVPPVVHG (1b) (SEQ ID NO:64) |
| | | | PDYQPATVAG (2a) (SEQ ID NO:61) |
| | | | PGYEPPTVLG (2b) (SEQ ID NO:65) |
| (2) FF25912 (1a) | 6.44 | cp402-00 (1a) | |
| | 4.38 | cp402-01 (1b) | |
| | 5.52 | cp402-02 (2a) | |
| | 5.30 | cp402-03 (2b) | |
| Non-type specific (conserved) epitopes | | | WARPDYN (SEQ ID NO:40) |

TABLE 14

Serotyping Epitope Analysis from Different Types of HCV Sequences (I) Chronic NANBH from Paid Donors Sequence Region: NS5 (2281–2313)

| Sample ID (HCV Type) | Peptide EIA S/CO | Peptide | Type Dependent Sequences | | |
|---|---|---|---|---|---|
| (1) NAC5 (1b) | 7.28 | cp402-00 (1a) | FAQALPVWARPDYNPPLVETWKK | PDYEPPVVHG | (SEQ ID NO:56) |
| | 6.59 | cp402-01 (1b) | FPPALPIWARPDYNPPLLESWKD | PDYVPPVVHG | (SEQ ID NO:57) |
| | 0.10 | cp402-02 (2a) | FPPALPAWARPDYNPPLVESWKR | PDYQPATVAG | (SEQ ID NO:58) |
| | 0.47 | cp402-03 (2b) | FPPALPPWARPDYNPVLIETWKR | PGYEPPTVLG | (SEQ ID NO:59) |
| | | | Type specific epitope (1a & 1b) | PDYEPPVVHG (1a) | (SEQ ID NO:63) |
| | 6.36 | r-NS5ELISA | | PDYVPPVVHG (1b) | (SEQ ID NO:64) |
| | | | | PDYQPATVAG (2a) | (SEQ ID NO:61) |
| | | | | PGYEPPTVLG (2b) | (SEQ ID NO:65) |
| | | | | * * * * | |
| (2) W1 (1a) | 7.80 | cp402-00 (1a) | Type specific epitope (1a & 1b) | PDYEPPVVHG (1a) | (SEQ ID NO:63) |
| | 5.43 | cp402-01 (1b) | | PDYVPPVVHG (1b) | (SEQ ID NO:64) |
| | 0.56 | cp402-02 (2a) | | | |
| | 0.58 | cp402-03 (2b) | | | |
| | 6.86 | r-NS5ELISA (1a) | | | |
| (3) MT56 (1a & 1b) | 7.68 | cp402-00 (1a) | | | |
| | 7.39 | cp402-01 (1b) | | | |
| | 5.07 | cp402-02 (2a) | P* V I | PDYQPATVAG | (SEQ ID NO:61) |
| | 0.36 | cp402-03 (2b) | | | |
| | 6.89 | r-NS5 ELISA | | | |

EXAMPLE 6

Inhibition Assay

The inhibition assays were performed to determine whether the peptides could compete with each other for binding to antibodies. Three sets of short polypeptides from the core NS4 and NS5 regions of different types of HCV sequences were synthesized. These polypeptides cover the sequence regions from amino acid 1689–1695, 1696–1702 and 1711–1717. The inhibition assays were performed by addition of 10 μg of the above polypeptides to the sample and incubation at 37° C. for one hour and then performance of the ELISA assays as described above. If inhibition was found to be more than 50% of antibody binding, the polypeptide was considered to be inhibitory. The results obtained are presented in the following Table.

TABLE 15

Inhibition Analysis

| Polypeptide | Region | Amino Acids | Virus type Inhibition |
|---|---|---|---|
| 1. SQHLPY (SEQ ID NO:66) CHIEN-101 | NS4 Region | 1712–1717 | 1a |
| 2. ASRAAL (SEQ ID NO:67) CHIEN-102 | | 1712–1717 | 2a |
| 3. ASKAAL (SEQ ID NO:68) CHIEN-103 | | 1712–1717 | 2b |
| 4. PDREVLY (SEQ ID NO:69) CHIEN-104 | | 1696–1972 | 1a, 1b, 2a |
| 5. PDYRPPVVHG (SEQ ID NO:70) CHIEN-105 | NS5 Region | 2304–2313 | 1a |
| 6. PDYQPATVAG (SEQ ID NO:71) CHIEN-106 | | 2304–2313 | 2a |
| 7. FAQALPVW (SEQ ID NO:72) CHIEN-107 | | 2281–2288 | 1a |
| 8. FPPQALPPW (SEQ ID NO:73) CHIEN-108 | | 2281–2288 | 2b |
| 9. STGKSWGK (SEQ ID NO:74) CHIEN-109 | Core | 71–78 | 2a & 2b |
| 10. SEGRSWAQ (SEQ ID NO:75) CHIEN-110 | Core | 71–78 | 4 |

TABLE 16

HCV Major Type Specific Epitopes in Core, NS4 & NS5 Regions

| Major Conserved Epitopes | Type Specific Epitopes | | Conserved Epitopes |
|---|---|---|---|
| Core Region: (15–45) | (67–84) | | (67–84) |
| TNRRPQDVKFPGGGQIVGGVY LLPRRGPRLG (HCV-1) (SEQ ID NO:30) | HCV-1a & 1b HCV-2a & 2b HCV-3a or 4 | PEGRTWAQ (SEQ ID NO:31) STGKSWGK (SEQ ID NO:33) SEGRSWAQ (SEQ ID NO:34) | PGYPWP (SEQ ID NO:32) (1a,1b,2a,2b,3a) F (4) |
| NS4 Region: (1925–1935) | (1689–1718) | | (1689–1718) |
| RGNHVSPTHYV (HCV-1) (SEQ ID NO:35) | HCV-1a HCV-1b HCV-2a & 2b | CSQHLPY (SEQ ID NO:36) CASHLPY (SEQ ID NO:38) CASRAAL (SEQ ID NO:39) K | PDREVLY (SEQ ID NO:37)(1a,1b) K I (2a,2b) |
| NS5 Region: (2288–2294) | (2281–2313) | | |
| WARPDYN (SEQ ID NO:40) | HCV-1a & 1b | PDYEPPVVHG (SEQ ID NO:41) V | |
| | HCV-2a HCV-2b | PDYQPATVAG (SEQ ID NO:42) PGYEPPTVLG (SEQ ID NO:43) | |
| | HCV-1a | FAQALPVW (SEQ ID NO:44) | |
| | HCV-1b,2a&2b | FPPQALPIW (SEQ ID NO:45) A P | |
| (2673–2707) | | | |
| RGENCGYRRCRASGVLTT HCV-1a (SEQ ID NO:46) K QT (SEQ ID NO:47) HCV-1b,2a K QS (SEQ ID NO:48) HCV-3b | KGAQCGYRRCRASGVL P T--HCV-3a (SEQ ID NO:49) * KGQSCGYRRCRASGVFTT-HCV-2b * | | |

We claim:

1. A method for detecting one or more types of hepatitis C virus (HCV) in a sample, said method comprising the steps of:
   (a) providing a biological sample from an individual suspected of being infected by a hepatitis C virus;
   (b) contacting the sample with a first nucleic acid molecule wherein said first nucleic acid molecule encodes at least one first HCV epitope selected from the group consisting of an epitope within amino acid residues 67 to 84 of the core domain, relative to the HCV-1 viral polyprotein sequence; an epitope within amino acid residues 1689 to 1718 of the NS4 domain, relative to the HCV-1 viral polyprotein sequence; and an epitope within amino acid residues 2281 to 2313 the NS5 domain, relative to the HCV-1 viral polyprotein sequence; wherein said at least one first epitope is from 5 to 15 amino acids in length and wherein said first epitope is further selected from the group consisting of a first type-specific epitope specific for a first type of hepatitis C virus and a first type-cluster specific epitope specific for a first type-cluster of hepatitis C virus, under conditions that allow the selective hybridization of said nucleic acid molecule to a HCV polynucleotide or the complement thereof in said sample; and
   (c) determining whether polynucleotide duplexes comprising said first nucleic acid molecule are formed, where formation of such duplexes indicates detection of a first type or type-cluster of HCV in the sample;
   (d) contacting the samples containing said polynucleotide duplexes with a second nucleic acid molecule wherein said second nucleic acid molecule encodes at least one second HCV epitope different from said first HCV epitope, said at least one second epitope selected from the group consisting of an epitope within amino acids 67 to 84 of the core domain, relative to the HCV-1 viral polyprotein sequence; an epitope within amino acids 1689 to 1718 of the NS4 domain, relative to the HCV-1 viral polyprotein sequence; and an epitope within amino acids 2281 to 2313 of the NS5 domain, relative to the HCV-1 viral polyprotein sequence; wherein said at least one second epitope is from 5 to 15 amino acids in length and wherein said second epitope is further selected from the group consisting of a second type-specific epitope specific for a second type of hepatitis C virus and a second type-cluster specific epitope specific for a second type-cluster of hepatitis C virus, under conditions that allow the selective hybridization of said second nucleic acid molecule to a HCV polynucleotide or the complement thereof in said sample; and
   (e) determining whether polynucleotide duplexes comprising said second nucleic acid molecule are formed, where formation of such duplexes indicates detection of a second type or type-cluster of HCV in the sample.

2. The method according to claim 1, wherein said first epitope is from a region of the HCV core domain corresponding to amino acid 67 to amino acid 84 of hepatitis C virus-1.

3. The method according to claim 2, wherein said second epitope is from a region of the HCV NS4 domain corresponding to amino acid 1689 to amino acid 1718 of hepatitis C virus-1.

4. The method according to claim 2, wherein said second epitope is from a region of the HCV NS5 domain corresponding to amino acid 2281 to amino acid 2313 of hepatitis C virus-1.

5. The method according to claim 1, wherein said first epitope is from a region of the HCV NS4 domain corresponding to amino acid 1689 to amino acid 1718 of hepatitis C virus-1.

6. The method according to claim 5, wherein said second epitope is from a region of the HCV NS5 domain corresponding to amino acid 2281 to amino acid 2313 of hepatitis C virus-1.

7. A method for typing one or more types or type-clusters of a hepatitis C virus (HCV) in a sample, said method comprising the steps of:
(a) providing a biological sample from an individual suspected of being infected by a hepatitis C virus;

(b) contacting the sample with a first nucleic acid molecule wherein said first nucleic acid molecule encodes at least one first HCV epitope selected from the group consisting of an epitope within amino acids 67 to 84 of the core domain, relative to the HCV-1 viral polyprotein sequence; an epitope within amino acids 1689 to 1718 of the NS4 domain, relative to the HCV-1 viral polyprotein sequence; and an epitope within amino acids 2281 to 2313 of the NS5 domain, relative to the HCV-1 viral polyprotein sequence; wherein said at least one first epitope is from 5 to 15 amino acids in length and wherein said first epitope is further selected from the group consisting of a first type-specific epitope specific for a first type of hepatitis C virus and a first type-cluster specific epitope specific for a first type-cluster of hepatitis C virus, under conditions that allow the selective hybridization of said nucleic acid molecule to a HCV polynucleotide or the complement thereof in said sample; and (c) determining whether polynucleotide duplexes comprising said first nucleic acid molecule are formed, wherein the presence of said duplexes is indicative of a type or typecluster of HCV being present in the sample.

8. The method according go claim 7, wherein said first epitope is from a region of the HCV core domain corresponding to amino acid 67 to amino acid 84 of hepatitis C virus-1.

9. The method according to claim 7, wherein said first epitope is from a region of the HCV NS4 domain corresponding to amino acid 1689 to amino acid 1718 of hepatitis C virus-1.

10. The method according to claim 7, wherein said first epitope is from a region of the HCV NS5 domain corresponding to amino acid 2281 to amino acid 2313 of hepatitis C virus-1.

11. The method according to claim 7 further comprising the steps of:

(d) contacting the samples containing said polynucleotide duplexes with a second nucleic acid molecule wherein said second nucleic acid molecule encodes at least one second HCV epitope different from said first HCV epitope, said at least one second epitope selected from the group consisting of an epitope within amino acids 67 to 84 of the core domain, relative to the HCV-1 viral polyprotein sequence; an epitope within amino acids 1689 to 1718 of the NS4 domain, relative to the HCV-1 viral polyprotein sequence; and an epitope within amino acids 2281 to 2313 of the NS5 domain, relative to the HCV-1 viral polyprotein sequence; provided that the second epitope is selected from a region different from that of the first epitope, wherein said at least one second epitope is from 5 to 15 amino acids in length and wherein said second epitope is further selected from the group consisting of a second type-specific epitope specific for a second type of hepatitis C virus and a second type-cluster specific epitope specific for a second type-cluster of hepatitis C virus, under conditions that allow the selective hybridization of said nucleic acid molecule to a HCV polynucleotide or the complement thereof in said sample; and (e) determining whether polynucleotide duplexes comprising said second nucleic acid molecule are formed wherein said second duplexes are indicative of a type or type-cluster of HCV being present in the sample.

12. The method according to claim 11, wherein said first epitope is from a region of the HCV core domain corresponding to amino acid 67 to amino acid 84 of hepatitis C virus-1.

13. The method according to claim 12, wherein said second epitope is from a region of the HCV NS4 domain corresponding to amino acid 1689 to amino acid 1718 of hepatitis C virus-1.

14. The method according to claim 12, wherein said second epitope is from a region of the HCV NS5 domain corresponding to amino acid 2281 to amino acid 2313 of hepatitis C virus-1.

15. The method according to claim 11, wherein said first epitope is from a region of the HCV NS4 domain corresponding to amino acid 1689 to amino acid 1718 of hepatitis C virus-1.

16. The method according to claim 15, wherein said second epitope is from a region of the HCV NS5 domain corresponding to amino acid 2281 to amino acid 2313 of hepatitis C virus-1.

17. A method for typing one or more types or type-clusters of a hepatitis C virus comprising the steps of:

(a) providing a nucleic acid molecule capable of selectively hybridizing to a target region within a genome of a hepatitis C virus (HCV), or its complement, wherein the nucleic acid molecule encodes at least one first HCV epitope selected from the group consisting of an epitope within amino acids 67 to 84 of the core domain, relative to the HCV-1 viral polyprotein sequence; an epitope within amino acids 1689 to 1718 of the NS4 domain, relative to the HCV-1 viral polyprotein sequence; and an epitope within amino acids 2281 to 2313 of the NS5 domain, relative to the HCV-1 viral polyprotein sequence; wherein said at least one first epitope is from 5 to 15 amino acids in length and wherein said first epitope is further selected from the group consisting of a first type-specific epitope specific for a first type of hepatitis C virus and a first type-cluster specific epitope specific for a first type-cluster of hepatitis C virus, or its complement;

(b) providing a set of primer nucleic acid molecules which are primers for the polymerase chain reaction method and which flank the target region;

(c) amplifying the target region via a polymerase chain reaction method to obtain an amplified test sample;

(d) incubating the amplified test sample with the nucleic acid molecule of step (a) under conditions which allow hybrid duplexes to form between the nucleic acid molecule and the target region; and (e) detecting any hybrids formed between the target region and the nucleic acid molecule, wherein the presence of said hybrid duplex is indicative of a type or type-cluster of HCV being present in the test sample.

18. The method according to claim 17, wherein said first epitope is from a region of the HCV core domain corresponding to amino acid 67 to amino acid 84 of hepatitis C virus-1.

19. The method according to claim 17, wherein said first epitope is from a region of the HCV NS4 domain corresponding to amino acid 1689 to amino acid 1718 of hepatitis C virus-1.

20. The method according to claim 17, wherein said first epitope from a region of the HCV NS5 domain corresponding to amino acid 2281 to amino acid 2313 of hepatitis C virus-1.

21. The method according to claim 17 further comprising the steps of:
(f) providing a second nucleic acid molecule capable of selectively hybridizing to a second target region within a genome of a hepatitis C virus (HCV), or its complement, wherein the nucleic acid molecule encodes at least one second HCV epitope different from said first HCV epitope, said at least one second epitope selected from the group consisting of an epitope within amino acids 67 to 84 of the core domain, relative to the HCV-1 viral polyprotein sequence; an epitope within amino acids 1689 to 1718 of the NS4 domain, relative to the HCV-1 viral polyprotein sequence; and an epitope within amino acids 2281 to 2313 of the NS5 domain, relative to the HCV-1 viral polyprotein sequence; provided that the second epitope is selected from a region different from the first epitope, wherein said at least one second epitope is from 5 to 15 amino acids in length and wherein said second epitope is further selected from the group consisting of a second type-specific epitope specific for a second type of hepatitis C virus and a second type-cluster specific epitope specific for a second type-cluster of hepatitis C virus, or its complement;
(g) providing a second set of primer nucleic acid molecules which are primers for the polymerase chain reaction method and which flank the second target region;
(h) amplifying the second target region via a polymerase chain reaction method to obtain an amplified test sample;
(i) incubating the amplified test sample with the second nucleic acid molecule of step (f) under conditions which allow hybrid duplexes to form between the second nucleic acid molecule and the second target region; and
(j) detecting any hybrids formed between the second target region and the second nucleic acid molecule, wherein: the presence of said hybrid duplex is indicative of a second type or type-cluster of HCV being present in the test sample.

22. The according to claim 21, wherein said first epitope is from a region of the HCV core domain corresponding to amino acid 67 to amino acid 84 of hepatitis C virus-1.

23. The method according to claim 22, wherein said second epitope if from a region of the HCV NS4 domain corresponding to amino acid 1689 to amino acid 1718 of hepatitis C virus-1.

24. The method according to claim 22, wherein said second epitope if from a region of the HCV NS5 domain corresponding to amino acid 2281 to amino acid 2313 of hepatitis C virus-1.

25. The method according to claim 21, wherein said first epitope is from a region of the HCV NS4 domain corresponding to amino acid 1689 to amino acid 1718 of hepatitis C virus-1.

26. The method according to claim 25, wherein said second epitope is from a region of the HCV NS5 domain corresponding to amino acid 2281 to amino acid 2313 of hepatitis C virus-1.

* * * * *

```
                             SEQUENCE LISTING (1) GENERAL INFORMATION:

(iii) NUMBER OF SEQUENCES: 75

(2) INFORMATION FOR SEQ ID NO: 1:

(i) SEQUENCE CHARACTERISTICS:
        (A) LENGTH: 150 amino acids
        (B) TYPE: amino acid
        (C) STRANDEDNESS: single
        (D) TOPOLOGY: linear (xi) SEQUENCE DESCRIPTION: SEQ ID NO: 1:

Val Cys Ala Arg Ala Gln Ala Pro Pro Pro Ser Trp Asp Gln Met Trp
1               5                   10                  15

Lys Cys Leu Ile Arg Leu Lys Pro Thr Leu His Gly Pro Thr Pro Leu
            20                  25                  30

Leu Tyr Arg Leu Gly Ala Val Gln Asn Glu Ile Thr Leu Thr His Pro
        35                  40                  45

Val Thr Lys Tyr Ile Met Thr Cys Met Ser Ala Asp Leu Glu Val Val
    50                  55                  60

Thr Ser Thr Trp Val Leu Val Gly Gly Val Leu Ala Ala Leu Ala Ala
65                  70                  75                  80
```

```
Tyr Cys Leu Ser Thr Gly Cys Val Val Ile Val Gly Arg Val Val Leu
                85                  90                  95

Ser Gly Lys Pro Ala Ile Ile Pro Asp Arg Glu Val Leu Tyr Arg Glu
            100                 105                 110

Phe Asp Glu Met Glu Glu Cys Ser Gln His Leu Pro Tyr Ile Glu Gln
            115                 120                 125

Gly Met Met Leu Ala Glu Gln Phe Lys Gln Lys Ala Leu Gly Leu Leu
        130                 135                 140

Gln Thr Ala Ser Arg Gln
145                 150
```

(2) INFORMATION FOR SEQ ID NO: 2:

(i) SEQUENCE CHARACTERISTICS:
       (A) LENGTH: 155 amino acids
       (B) TYPE: amino acid
       (C) STRANDEDNESS: single
       (D) TOPOLOGY: linear (xi) SEQUENCE DESCRIPTION: SEQ ID NO: 2:

```
Val Cys Ala Arg Ala Lys Ala Pro Pro Ser Trp Asp Val Met Trp
1               5                   10                  15

Lys Cys Leu Ala Arg Leu Lys Pro Thr Leu Ile Gly Pro Thr Pro Leu
            20                  25                  30

Leu Tyr Arg Leu Gly Ala Val Thr Asn Glu Val Thr Leu Thr His Pro
            35                  40                  45

Val Thr Lys Thr Ile Ala Thr Cys Met Ser Val Asn Leu Glu Ile Met
        50                  55                  60

Thr Ser Thr Trp Val Leu Ala Gly Gly Val Leu Ala Ala Val Ala Ala
65                  70                  75                  80

Tyr Cys Leu Ala Thr Gly Cys Val Ser Ile Ile Gly Arg Leu His Leu
                85                  90                  95

Asn Asp Gln Val Val Val Thr Pro Asp Lys Glu Ile Leu Tyr Glu Ala
            100                 105                 110

Phe Asp Glu Met Glu Glu Cys Ala Ser Lys Ala Ala Leu Ile Glu Glu
            115                 120                 125

Gly Gln Arg Met Ala Glu Met Leu Lys Ser Lys Ile Gln Gly Leu Leu
        130                 135                 140

Gln Gln Ala Thr Arg Gln Ala Gln Asp Ile Gln
145                 150                 155
```

(2) INFORMATION FOR SEQ ID NO: 3:

(i) SEQUENCE CHARACTERISTICS:
       (A) LENGTH: 8 amino acids
       (B) TYPE: amino acid
       (C) STRANDEDNESS: single
       (D) TOPOLOGY: linear (xi) SEQUENCE DESCRIPTION: SEQ ID NO: 3:

```
Pro Glu Gly Arg Thr Trp Ala Gln
1               5
```

(2) INFORMATION FOR SEQ ID NO: 4:

(i) SEQUENCE CHARACTERISTICS:
       (A) LENGTH: 8 amino acids
       (B) TYPE: amino acid
       (C) STRANDEDNESS: single
       (D) TOPOLOGY: linear (xi) SEQUENCE DESCRIPTION: SEQ ID NO: 4:

Ser Thr Gly Lys Ser Trp Gly Lys
1               5

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 5:

Ser Glu Gly Arg Ser Trp Ala Gln
1               5

(2) INFORMATION FOR SEQ ID NO: 6:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 6:

Cys Ser Gln His Leu Pro Tyr
1               5

(2) INFORMATION FOR SEQ ID NO: 7:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 7:

Cys Ala Ser His Leu Pro Tyr
1               5

(2) INFORMATION FOR SEQ ID NO: 8:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 8:

Cys Ala Ser Arg Ala Ala Leu
1               5

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 9:

Pro Asp Tyr Glu Pro Pro Val Val His Gly
1               5                   10

(2) INFORMATION FOR SEQ ID NO: 10:

(i) SEQUENCE CHARACTERISTICS:

```
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 10:

Pro Asp Tyr Val Pro Pro Val Val His Gly
1               5                   10

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 11:

Pro Asp Tyr Gln Pro Ala Thr Val Ala Gly
1               5                   10

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 12:

Pro Gly Tyr Glu Pro Pro Thr Val Leu Gly
1               5                   10

(2) INFORMATION FOR SEQ ID NO: 13:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 13:

Phe Ala Gln Ala Ser Pro Val Trp
1               5

(2) INFORMATION FOR SEQ ID NO: 14:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 14:

Phe Pro Pro Gln Ala Leu Pro Ile Trp
1               5

(2) INFORMATION FOR SEQ ID NO: 15:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 15:

Phe Pro Pro Gln Ala Leu Pro Ala Trp
1               5
```

(2) INFORMATION FOR SEQ ID NO: 16:

(i) SEQUENCE CHARACTERISTICS:
       (A) LENGTH: 9 amino acids
       (B) TYPE: amino acid
       (C) STRANDEDNESS: single
       (D) TOPOLOGY: linear (xi) SEQUENCE DESCRIPTION: SEQ ID NO: 16:

Phe Pro Pro Gln Ala Leu Pro Pro Trp
1               5

(2) INFORMATION FOR SEQ ID NO: 17:

(i) SEQUENCE CHARACTERISTICS:
       (A) LENGTH: 30 amino acids
       (B) TYPE: amino acid
       (C) STRANDEDNESS: single
       (D) TOPOLOGY: linear (xi) SEQUENCE DESCRIPTION: SEQ ID NO: 17:

Ser Gly Lys Pro Ala Ile Ile Pro Asp Arg Glu Val Leu Tyr Arg Glu
1               5                   10                  15

Phe Asp Glu Met Glu Glu Cys Ser Gln His Leu Pro Tyr Ile
            20                  25                  30

(2) INFORMATION FOR SEQ ID NO: 18:

(i) SEQUENCE CHARACTERISTICS:
       (A) LENGTH: 29 amino acids
       (B) TYPE: amino acid
       (C) STRANDEDNESS: single
       (D) TOPOLOGY: linear (xi) SEQUENCE DESCRIPTION: SEQ ID NO: 18:

Ser Gly Arg Pro Ala Val Ile Pro Asp Arg Glu Val Leu Tyr Gln Phe
1               5                   10                  15

Asp Glu Met Glu Glu Cys Ala Ser His Leu Pro Tyr Ile
            20                  25

(2) INFORMATION FOR SEQ ID NO: 19:

(i) SEQUENCE CHARACTERISTICS:
       (A) LENGTH: 30 amino acids
       (B) TYPE: amino acid
       (C) STRANDEDNESS: single
       (D) TOPOLOGY: linear (xi) SEQUENCE DESCRIPTION: SEQ ID NO: 19:

Asn Gln Arg Ala Val Val Ala Pro Asp Lys Glu Val Leu Tyr Glu Ala
1               5                   10                  15

Phe Asp Glu Met Glu Glu Cys Ala Ser Arg Ala Ala Leu Ile
            20                  25                  30

(2) INFORMATION FOR SEQ ID NO: 20:

(i) SEQUENCE CHARACTERISTICS:
       (A) LENGTH: 30 amino acids
       (B) TYPE: amino acid
       (C) STRANDEDNESS: single
       (D) TOPOLOGY: linear (xi) SEQUENCE DESCRIPTION: SEQ ID NO: 20:

Asn Asp Arg Val Val Val Ala Pro Asp Lys Glu Ile Leu Tyr Glu Ala
1               5                   10                  15

```
Phe Asp Glu Met Glu Glu Cys Ala Ser Lys Ala Ala Leu Ile
            20                  25                  30
```

(2) INFORMATION FOR SEQ ID NO: 21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /note= "This position is either R
            or K."

(ix) FEATURE:
        (A) NAME/KEY: Modified-site
        (B) LOCATION: 5
        (D) OTHER INFORMATION: /note= "This position is either V
            or I."

(xi) SEQUENCE DESCRIPTION: SEQ ID NO: 21:

```
Pro Asp Xaa Glu Xaa Leu Tyr
1               5
```

(2) INFORMATION FOR SEQ ID NO: 22:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 22:

```
Cys Ala Ser Arg Ala Ala Leu
1               5
```

(2) INFORMATION FOR SEQ ID NO: 23:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 23:

```
Cys Ala Ser Lys Ala Ala Leu
1               5
```

(2) INFORMATION FOR SEQ ID NO: 24:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO: 24:

```
Ile Lys Ser Leu Thr Glu Arg Leu Tyr Val Gly Gly Pro Leu Thr Asn
1               5                   10                  15
Ser Arg Gly Glu Asn Cys Gly Tyr Arg Arg Cys Arg Ala Ser Gly Val
            20                  25                  30
Leu Thr Thr
        35
```

```
(2) INFORMATION FOR SEQ ID NO: 25:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO: 25:

Ile His Ser Leu Thr Glu Arg Leu Tyr Val Gly Gly Pro Met Phe Asn
1               5                   10                  15

Ser Lys Gly Gln Thr Cys Gly Tyr Arg Arg Cys Arg Ala Ser Gly Val
                20                  25                  30

Leu Thr Thr
        35

(2) INFORMATION FOR SEQ ID NO: 26:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO: 26:

Ile His Ser Leu Thr Glu Arg Leu Tyr Val Gly Gly Pro Met Phe Asn
1               5                   10                  15

Ser Lys Gly Gln Thr Cys Gly Tyr Arg Arg Cys Arg Ala Ser Gly Val
                20                  25                  30

Leu Thr Thr
        35

(2) INFORMATION FOR SEQ ID NO: 27:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO: 27:

Ile Ser Ser Leu Thr Glu Arg Leu Tyr Val Gly Gly Pro Met Phe Asn
1               5                   10                  15

Ser Lys Gly Gln Ser Cys Gly Tyr Arg Arg Cys Arg Ala Ser Gly Val
                20                  25                  30

Leu Thr Thr
        35

(2) INFORMATION FOR SEQ ID NO: 28:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO: 28:

Ile His Ser Leu Thr Glu Arg Leu Tyr Val Gly Gly Pro Met Thr Asn
1               5                   10                  15

Ser Lys Gly Gln Ser Cys Gly Tyr Arg Arg Cys Arg Ala Ser Gly Val
                20                  25                  30

Phe Thr Thr
        35
```

(2) INFORMATION FOR SEQ ID NO: 29:

(i) SEQUENCE CHARACTERISTICS:
        (A) LENGTH: 35 amino acids
        (B) TYPE: amino acid
        (C) STRANDEDNESS: single
        (D) TOPOLOGY: linear (xi) SEQUENCE DESCRIPTION: SEQ ID NO: 29:

```
Ile Ser Ser Leu Thr Glu Arg Leu Tyr Cys Gly Gly Pro Met Phe Asn
1               5                   10                  15

Ser Lys Gly Ala Gln Cys Gly Tyr Arg Arg Cys Arg Ala Ser Gly Val
            20                  25                  30

Leu Pro Thr
        35
```

(2) INFORMATION FOR SEQ ID NO: 30:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 30:

```
Thr Asn Arg Arg Pro Gln Asp Val Lys Phe Pro Gly Gly Gly Gln Ile
1               5                   10                  15

Val Gly Gly Val Tyr Leu Leu Pro Arg Arg Gly Pro Arg Leu Gly
            20                  25                  30
```

(2) INFORMATION FOR SEQ ID NO: 31:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 31:

```
Pro Glu Gly Arg Thr Trp Ala Gln
1               5
```

(2) INFORMATION FOR SEQ ID NO: 32:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 32:

```
Pro Gly Tyr Pro Trp Pro
1               5
```

(2) INFORMATION FOR SEQ ID NO: 33:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 33:

```
Ser Thr Gly Lys Ser Trp Gly Lys
1               5
```

(2) INFORMATION FOR SEQ ID NO: 34:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 34:

Ser Glu Gly Arg Ser Trp Ala Gln
1          5

(2) INFORMATION FOR SEQ ID NO: 35:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO: 35:

Arg Gly Asn His Val Ser Pro Thr His Tyr Val
1          5                 10

(2) INFORMATION FOR SEQ ID NO: 36:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 36:

Cys Ser Gln His Leu Pro Tyr
1          5

(2) INFORMATION FOR SEQ ID NO: 37:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 3
        (D) OTHER INFORMATION: /note= "This position is R or K."

(ix) FEATURE:
        (A) NAME/KEY: Modified-site
        (B) LOCATION: 5
        (D) OTHER INFORMATION: /note= "This position is V or I."

(xi) SEQUENCE DESCRIPTION: SEQ ID NO: 37:

Pro Asp Xaa Glu Xaa Leu Tyr
1          5

(2) INFORMATION FOR SEQ ID NO: 38:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 38:

Cys Ala Ser His Leu Pro Tyr
1          5

(2) INFORMATION FOR SEQ ID NO: 39:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 4
        (D) OTHER INFORMATION: /note= "This position is R or K."

(xi) SEQUENCE DESCRIPTION: SEQ ID NO: 39:

Cys Ala Ser Xaa Ala Ala Leu
1            5

(2) INFORMATION FOR SEQ ID NO: 40:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 40:

Trp Ala Arg Pro Asp Tyr Asn
1            5

(2) INFORMATION FOR SEQ ID NO: 41:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 4
        (D) OTHER INFORMATION: /note= "This position is E or V."

(xi) SEQUENCE DESCRIPTION: SEQ ID NO: 41:

Pro Asp Tyr Xaa Pro Pro Val Val His Gly
1            5                    10

(2) INFORMATION FOR SEQ ID NO: 42:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 42:

Pro Asp Tyr Gln Pro Ala Thr Val Ala Gly
1            5                    10

(2) INFORMATION FOR SEQ ID NO: 43:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 43:

Pro Gly Tyr Glu Pro Pro Thr Val Leu Gly

```
1               5                   10
```

(2) INFORMATION FOR SEQ ID NO: 44:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 44:

```
Phe Ala Gln Ala Leu Pro Val Trp
1               5
```

(2) INFORMATION FOR SEQ ID NO: 45:

(i) SEQUENCE CHARACTERISTICS:
        (A) LENGTH: 9 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 8
        (D) OTHER INFORMATION: /note= "This position is I or A or
            P."

(xi) SEQUENCE DESCRIPTION: SEQ ID NO: 45:

```
Phe Pro Pro Gln Ala Leu Pro Xaa Trp
1               5
```

(2) INFORMATION FOR SEQ ID NO: 46:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 46:

```
Arg Gly Glu Asn Cys Gly Tyr Arg Arg Cys Arg Ala Ser Gly Val Leu
1               5                   10                  15
Thr Thr
```

(2) INFORMATION FOR SEQ ID NO: 47:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 47:

```
Lys Gly Gln Thr Cys Gly Tyr Arg Arg Cys Arg Ala Ser Gly Val Leu
1               5                   10                  15
Thr Thr
```

(2) INFORMATION FOR SEQ ID NO: 48:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 48:

```
Lys Gly Gln Ser Cys Gly Tyr Arg Arg Cys Arg Ala Ser Gly Val Leu
1               5                   10                  15

Thr Thr
```

(2) INFORMATION FOR SEQ ID NO: 49:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 49:

```
Lys Gly Ala Gln Cys Gly Tyr Arg Arg Cys Arg Ala Ser Gly Val Leu
1               5                   10                  15

Pro Thr
```

(2) INFORMATION FOR SEQ ID NO: 50:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 50:

```
Lys Gly Gln Ser Cys Gly Tyr Arg Arg Cys Arg Ala Ser Gly Val Phe
1               5                   10                  15

Thr Thr
```

(2) INFORMATION FOR SEQ ID NO: 51:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 51:

```
Lys Ala Arg Arg Pro Glu Gly Arg Thr Trp Ala Gln Pro Gly Tyr Pro
1               5                   10                  15

Trp Pro
```

(2) INFORMATION FOR SEQ ID NO: 52:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 52:

```
Lys Asp Arg Arg Ser Thr Gly Lys Ser Trp Gly Lys Pro Gly Tyr Pro
1               5                   10                  15

Trp Pro
```

(2) INFORMATION FOR SEQ ID NO: 53:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 53:

```
Lys Ala Arg Arg Ser Glu Gly Arg Ser Trp Ala Gln Pro Gly Tyr Pro
1               5                  10                 15

Trp Pro
```

(2) INFORMATION FOR SEQ ID NO: 54:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO: 54:

```
Lys Ala Arg Arg Ser Glu Gly Arg Ser Trp Ala Gln Pro Gly Phe Pro
1               5                  10                 15

Trp Pro
```

(2) INFORMATION FOR SEQ ID NO: 55:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 55:

```
Ser Thr Gly Lys Ser Trp Gly Lys
1               5
```

(2) INFORMATION FOR SEQ ID NO: 56:

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO: 56:

```
Phe Ala Gln Ala Leu Pro Val Trp Ala Arg Pro Asp Tyr Asn Pro Pro
1               5                  10                 15

Leu Val Glu Thr Trp Lys Lys Pro Asp Tyr Glu Pro Pro Val Val His
                20                  25                 30

Gly
```

(2) INFORMATION FOR SEQ ID NO: 57:

(i) SEQUENCE CHARACTERISTICS:
        (A) LENGTH: 66 amino acids
        (B) TYPE: amino acid
        (C) STRANDEDNESS: single
        (D) TOPOLOGY: linear (xi) SEQUENCE DESCRIPTION: SEQ ID NO: 57:

```
Phe Pro Pro Ala Leu Pro Ile Trp Ala Arg Pro Asp Tyr Asn Pro Pro
1               5                  10                 15

Leu Leu Glu Ser Trp Lys Asp Pro Asp Tyr Val Pro Pro Val Val His
                20                  25                 30

Gly Phe Pro Pro Ala Leu Pro Ile Trp Ala Arg Pro Asp Tyr Asn Pro
                35                  40                 45

Pro Leu Leu Glu Ser Trp Lys Asp Pro Asp Tyr Val Pro Pro Val Val
        50                  55                  60

His Gly
```

(2) INFORMATION FOR SEQ ID NO: 58:

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO: 58:

```
Phe Pro Pro Ala Leu Pro Ala Trp Ala Arg Pro Asp Tyr Asn Pro Pro
1               5                   10                  15

Leu Val Glu Ser Trp Lys Arg Pro Asp Tyr Gln Pro Ala Thr Val Ala
            20                  25                  30

Gly
```

(2) INFORMATION FOR SEQ ID NO: 59:

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO: 59:

```
Phe Pro Pro Ala Leu Pro Pro Trp Ala Arg Pro Asp Tyr Asn Pro Val
1               5                   10                  15

Leu Ile Glu Thr Trp Lys Arg Pro Gly Tyr Glu Pro Pro Thr Val Leu
            20                  25                  30

Gly
```

(2) INFORMATION FOR SEQ ID NO: 60:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 60:

```
Phe Ala Gln Ala Leu Pro Val Trp
1               5
```

(2) INFORMATION FOR SEQ ID NO: 61:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 61:

```
Pro Asp Tyr Gln Pro Ala Thr Val Ala Gly
1               5                   10
```

(2) INFORMATION FOR SEQ ID NO: 62:

(i) SEQUENCE CHARACTERISTICS:
        (A) LENGTH: 33 amino acids
        (B) TYPE: amino acid
        (C) STRANDEDNESS: single
        (D) TOPOLOGY: linear (xi) SEQUENCE DESCRIPTION: SEQ ID NO: 62:

```
Phe Pro Pro Ala Leu Pro Ala Trp Ala Arg Pro Asp Tyr Asn Pro Pro
1               5                   10                  15

Leu Leu Glu Ser Trp Lys Arg Pro Asp Tyr Gln Pro Ala Thr Val Ala
                20                  25                  30

Gly
```

(2) INFORMATION FOR SEQ ID NO: 63:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 63:

```
Pro Asp Tyr Glu Pro Pro Val Val His Gly
1               5                   10
```

(2) INFORMATION FOR SEQ ID NO: 64:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 64:

```
Pro Asp Tyr Val Pro Pro Val Val His Gly
1               5                   10
```

(2) INFORMATION FOR SEQ ID NO: 65:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 65:

```
Pro Gly Tyr Glu Pro Pro Thr Val Leu Gly
1               5                   10
```

(2) INFORMATION FOR SEQ ID NO: 66:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 66:

```
Ser Gln His Leu Pro Tyr
1               5
```

(2) INFORMATION FOR SEQ ID NO: 67:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 67:

```
Ala Ser Arg Ala Ala Leu
1               5
```

(2) INFORMATION FOR SEQ ID NO: 68:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 68:

```
Ala Ser Lys Ala Ala Leu
1               5
```

(2) INFORMATION FOR SEQ ID NO: 69:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 69:

```
Pro Asp Tyr Arg Pro Pro Val Val His Gly
1               5                   10
```

(2) INFORMATION FOR SEQ ID NO: 70:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 70:

```
Pro Asp Tyr Arg Pro Pro Val Val His Gly
1               5                   10
```

(2) INFORMATION FOR SEQ ID NO: 71:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 71:

```
Pro Asp Tyr Gln Pro Ala Thr Val Ala Gly
1               5                   10
```

(2) INFORMATION FOR SEQ ID NO: 72:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 72:

```
Phe Ala Gln Ala Leu Pro Val Trp
1               5
```

(2) INFORMATION FOR SEQ ID NO: 73:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 73:

-continued

```
Phe Pro Pro Gln Ala Leu Pro Pro Trp
1               5

(2) INFORMATION FOR SEQ ID NO: 74:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 74:

Ser Thr Gly Lys Ser Trp Gly Lys
1               5

(2) INFORMATION FOR SEQ ID NO: 75:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 75:

Ser Glu Gly Arg Ser Trp Ala Gln
1               5
```